(12) United States Patent
Yamaki et al.

(10) Patent No.: US 11,773,536 B2
(45) Date of Patent: *Oct. 3, 2023

(54) METHOD FOR PRODUCING PULP FIBRES FOR SACCHARIFICATION, AND AQUEOUS SOLUTION OF PULP FIBRES FOR SACCHARIFICATION

(71) Applicant: UNICHARM CORPORATION, Ehime (JP)

(72) Inventors: Kouichi Yamaki, Kanonji (JP); Takayoshi Konishi, Kanonji (JP); Naoto Ohashi, Kanonji (JP); Toshio Hiraoka, Kanonji (JP); Noritomo Kurita, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 667 days.

This patent is subject to a terminal disclaimer.

(21) Appl. No.: 16/624,957

(22) PCT Filed: May 10, 2018

(86) PCT No.: PCT/JP2018/018179
§ 371 (c)(1),
(2) Date: Dec. 20, 2019

(87) PCT Pub. No.: WO2019/003656
PCT Pub. Date: Jan. 3, 2019

(65) Prior Publication Data
US 2020/0141055 A1    May 7, 2020

(30) Foreign Application Priority Data
Jun. 28, 2017  (JP) ................. 2017-126789

(51) Int. Cl.
*D21C 5/02* (2006.01)
*A61F 13/53* (2006.01)
(Continued)

(52) U.S. Cl.
CPC .............. *D21C 5/022* (2013.01); *A61F 13/53* (2013.01); *A61L 2/18* (2013.01); *A61L 2/202* (2013.01);
(Continued)

(58) Field of Classification Search
None
See application file for complete search history.

(56) References Cited

U.S. PATENT DOCUMENTS 4,657,633 A * 4/1987 Dwiggins ............ D21C 9/1026
162/65
5,492,633 A * 2/1996 Moniwa .................... C02F 1/78
210/908
(Continued)

FOREIGN PATENT DOCUMENTS

EP         3238840 A1    11/2017
JP    2000167363 A  *  6/2000
(Continued)

OTHER PUBLICATIONS

English translation of JP-2000248482-A retrieved from Espaceneton Jan. 24, 2023 (Year: 2023).*
(Continued)

*Primary Examiner* — Eric Hug
*Assistant Examiner* — Elisa H Vera
(74) *Attorney, Agent, or Firm* — Fredrikson & Byron, P.A.

(57) ABSTRACT

The purpose of the present disclosure is to provide a method for producing pulp fibres for saccharification from the pulp fibres of used sanitary items, said pulp fibres for sacchari-
(Continued)

fication having low lignin contents distributed within a narrow range, and enabling the production of pulp fibres for saccharification having superior saccharification properties. The production method according to the present disclosure is characterised by comprising the following: a step for supplying a mixed solution (51) containing pulp fibres and highly-absorbent polymers sourced from used sanitary items to a treatment tank (31) via a mixed-solution supply port (32); a step for supplying an ozone-containing gas (53) to a treatment solution (52) within the treatment tank (31) via an ozone-containing-gas supply port (43); a step for lifting the ozone-containing gas (53) whilst lowering the pulp fibres and highly-absorbent polymers within the treatment tank (31), thereby bringing the ozone-containing gas (53) into contact with the pulp fibres and highly-absorbent polymers, and forming pulp fibres for saccharification from the pulp fibres; and a step for discharging the treatment solution (52) via a treatment-solution discharge port (33). The method is further characterised in that the pulp fibres for saccharification have lignin contents of 0.1% or less.

13 Claims, 3 Drawing Sheets

(51) Int. Cl.
A61L 2/18 (2006.01)
A61L 2/20 (2006.01)
A61L 11/00 (2006.01)
B29B 17/02 (2006.01)
D21H 11/14 (2006.01)
D21H 11/20 (2006.01)
B29L 31/48 (2006.01)
B09B 3/00 (2022.01)
B09B 3/80 (2022.01)

(52) U.S. Cl.
CPC ............ *A61L 11/00* (2013.01); *B09B 3/0075* (2013.01); *B09B 3/80* (2022.01); *B29B 17/02* (2013.01); *D21H 11/14* (2013.01); *D21H 11/20* (2013.01); *A61F 2013/530116* (2013.01); *B29B 2017/0293* (2013.01); *B29L 2031/4878* (2013.01)

(56) References Cited

U.S. PATENT DOCUMENTS

| | | | | |
|---|---|---|---|---|
| 6,238,516 | B1* | 5/2001 | Watson | B08B 3/045 162/57 |
| 2007/0227979 | A1* | 10/2007 | Kitagawa | D21C 11/0007 210/705 |
| 2009/0264036 | A1* | 10/2009 | Yano | H05K 1/0366 162/1 |
| 2010/0133197 | A1 | 6/2010 | Langner | |
| 2010/0159522 | A1* | 6/2010 | Cirakovic | C12P 19/14 536/128 |
| 2015/0291762 | A1* | 10/2015 | Watanabe | A61F 13/15707 428/401 |
| 2015/0307908 | A1* | 10/2015 | Quinlan | C07K 14/385 435/125 |
| 2016/0237617 | A1* | 8/2016 | Yamaguchi | D21C 3/04 |
| 2017/0107667 | A1 | 4/2017 | Konishi et al. | |
| 2017/0305037 | A1 | 10/2017 | Konishi et al. | |

FOREIGN PATENT DOCUMENTS

| | | | | |
|---|---|---|---|---|
| JP | 2000248482 | A | * | 9/2000 |
| JP | 200687319 | A | | 4/2006 |
| JP | 2006141244 | A | | 6/2006 |
| JP | 2009183211 | A | | 8/2009 |
| JP | 201017084 | A | | 1/2010 |
| JP | 201036058 | A | | 2/2010 |
| JP | 2013202021 | A | | 10/2013 |
| JP | 2016123973 | A | | 7/2016 |
| JP | 2016214218 | A | | 12/2016 |
| WO | WO-9417238 | A1 | * | 8/1994 ........... D21C 9/1026 |
| WO | 2015190140 | A1 | | 12/2015 |
| WO | 2016059964 | A1 | | 4/2016 |

OTHER PUBLICATIONS

English machine translation of JP2000167363A supplied by the Applicant (Year: 2023).*
English Abstract for Japanese Publication No. JP 2016-123973A, published Jul. 11, 2016, 1 pgs.
Extended European Search Report for European Patent Application No. 18823914.9, dated Apr. 8, 2020, 8 pgs.
PCT International Search Report dated Aug. 14, 2018 for Intl. App. No. PCT/JP2018/018179, from which the instant application is based, 2 pgs.
Abstracts of the 61st Annual Meeting of the Japan Wood Research Society, vol. 61s, Q19-P-AM17, Mar. 18-20, 2011), with English Translation, 5 pgs.
English Abstract and MachineTranslation for Japanese Publication No. 2013202021 A, published Oct. 7, 2013,14 pgs.
English Abstract and Machine Translation for Japanese Publication No. 2006141244 A, published Aug. 8, 2006, 27 pgs.
English Abstract and MachineTranslation for Japanese Publication No. 2009183211 A, published Aug. 20, 2009, 36 pgs.
English Abstract and MachineTranslation for Japanese Publication No. 2010017084 A, published Jan. 28, 2010, 30 pgs.
English Abstract and MachineTranslation for Japanese Publication No. 2010036058 A, published Feb. 18, 2010, 56 pgs.
English Abstract and MachineTranslation for Japanese Publication No. 2006087319 A, published Apr. 6, 2006, 27 pgs.
English Abstract and MachineTranslation for Japanese Publication No. 2016214218 A, published Dec. 22, 2016, 36 pgs.

* cited by examiner

METHOD FOR PRODUCING PULP FIBRES FOR SACCHARIFICATION, AND AQUEOUS SOLUTION OF PULP FIBRES FOR SACCHARIFICATION

RELATED APPLICATIONS

This application is a 35 U.S.C. 371 national stage filing from international application No. PCT/JP2018/018179, filed May 10, 2018, which claims priority to Japanese Application No. 2017-126789, filed Jun. 28, 2017, the teachings of which are incorporated herein by reference.

FIELD

The present disclosure relates to a method of manufacturing pulp fibers for saccharification from pulp fibers of used hygiene products, and to an aqueous solution of pulp fibers for saccharification which derives from used hygiene products including pulp fibers and super absorbent polymers.

BACKGROUND

Technologies for recycling hygiene products such as used disposable diapers, etc., have been studied.

For example, in Patent literature 1, a method of manufacturing recycled pulp which is reusable mainly as hygiene products is disclosed. More specifically, in Patent literature 1, a method of recovering pulp fibers from used hygiene products which include pulp fibers and super absorbent polymers, and manufacturing recycled pulp which is reusable as hygiene products, the method comprising: a step of disassembling the used hygiene products into pulp fibers and other materials, in an aqueous solution which includes polyvalent metal ions or an acidic aqueous solution with pH of 2.5 or lower, by applying physical force to the used hygiene products, a step of separating the pulp fibers from a mixture of the pulp fibers which is generated in the disassembling step and the other materials, and a step of treating the separated pulp fibers in an ozone containing aqueous solution with pH of 2.5 or lower, is described.

In Patent literature 1, the reason why the pulp fibers are treated with the ozone containing aqueous solution is that a considerable amount of the super absorbent polymers remains in the separated pulp fibers, and that the super absorbent polymers are oxidatively decomposed and are solubilized, whereby being removed from the pulp fibers. In Patent literature 1, as the method of treating the pulp fibers with the ozone containing aqueous solution, a method of putting the ozone containing aqueous solution in a treatment tank, and further putting the separated pulp fibers in the ozone containing aqueous solution is disclosed. In such a method, at the time of treatment, a water stream is preferably created by moderately stirring the ozone containing aqueous solution, or an ozone gas may be blown into an aqueous solution put in the container, and a water stream may be generated in the ozone containing aqueous solution by rising bubbles of ozone gas.

CITATION LIST

Patent Literature

[PTL 1] Japanese Unexamined Patent Publication No. 2013-202021

SUMMARY

Technical Problem

In Patent literature 1, a preferable manufacturing method of "recycled pulp fibers" which are reused as "pulp fibers for saccharification" is not described.

In used hygiene products, in absorbent bodies, etc., which include pulp fibers and super absorbent polymers, (i) as the super absorbent polymers absorb liquid, such as body fluid, etc., the super absorbent polymers enlarge and drag in the pulp fibers, and (ii) the enlarged super absorbent polymers cause gel blocking, etc., while dragging in the pulp fibers, whereby there are many cases in which a plurality of super absorbent polymers and a plurality of pulp fibers form a connected structure.

In such a case, it is discovered that although the method described in Patent literature 1 can disassemble the super absorbent polymers, etc., which configure the connected structure into a state of being able to be dissolved, however, the method is not necessarily preferable for the pulp fibers which configure the connected structure to be reused as a saccharification solution.

Accordingly, the object of the present disclosure is to provide a method of manufacturing pulp fibers for saccharification from pulp fibers in used hygiene products, which can manufacture pulp fibers for saccharification that have low lignin content ratio and narrow distribution thereof, and have excellent saccharification property.

Solution to Problem

The present inventors found out that a method of manufacturing pulp fibers for saccharification from pulp fibers of used hygiene products, comprising steps of: a preparation step of preparing a treatment tank which includes a liquid mixture supply port, and a treatment liquid discharge port and an ozone containing gas supply port that are arranged below the liquid mixture supply port, a liquid mixture supply step of supplying a liquid mixture which includes super absorbent polymers and the pulp fibers that derive from the used hygiene products and water, from the liquid mixture supply port to the treatment tank, an ozone containing gas supply step of supplying ozone containing gas from the ozone containing gas supply port to a treatment liquid in the treatment tank, a pulp fibers for saccharification formation step of forming the pulp fibers for saccharification from the pulp fibers while dissolving at least a portion of the super absorbent polymers in the treatment liquid, by, in the treatment tank, raising the ozone containing gas while lowering the super absorbent polymers and the pulp fibers so as to make the ozone containing gas come into contact with the super absorbent polymers and the pulp fibers, and a treatment liquid discharge step of discharging the treatment liquid which includes the pulp fibers for saccharification from the treatment liquid discharge port, wherein the pulp fibers for saccharification have a lignin content ratio of 0.1 mass % or less is the solution to the problem.

Advantageous Effects of Invention

The method of manufacturing pulp fibers for saccharification from pulp fibers in used hygiene products according to the present disclosure can manufacture pulp fibers for saccharification that have low lignin content ratio and narrow distribution thereof, and have excellent saccharification property.

DESCRIPTION OF EMBODIMENTS

Figure 1:
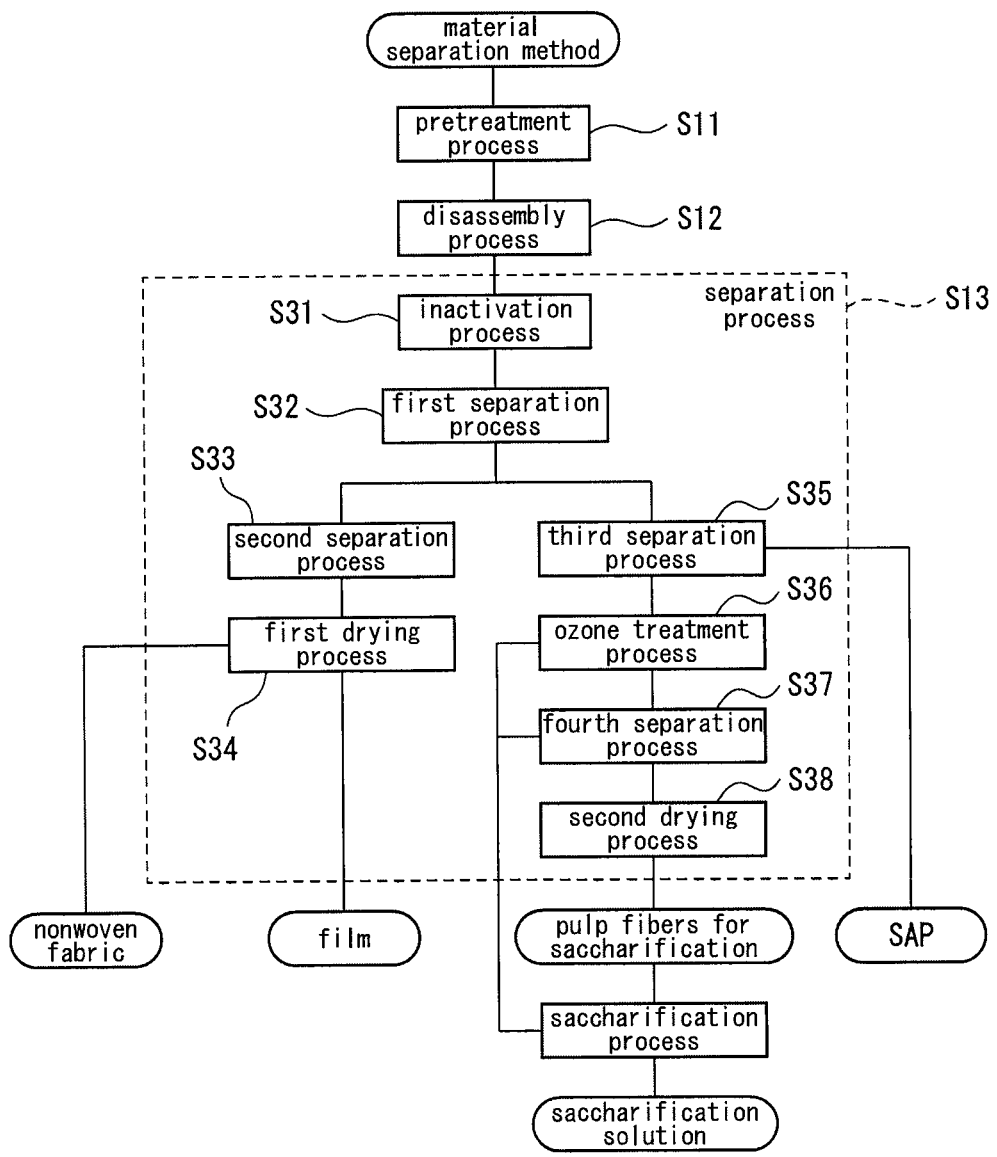
FIG. 1 is a flowchart which shows an embodiment of the method according to the present disclosure.

More specifically, the present disclosure relates to the following aspects.

[Aspect 1]

A method of manufacturing pulp fibers for saccharification from pulp fibers of used hygiene products, comprising steps of:

a preparation step of preparing a treatment tank which includes a liquid mixture supply port, and a treatment liquid discharge port and an ozone containing gas supply port that are arranged below the liquid mixture supply port, a liquid mixture supply step of supplying a liquid mixture which includes super absorbent polymers and the pulp fibers that derive from the used hygiene products and water, from the liquid mixture supply port to the treatment tank, an ozone containing gas supply step of supplying ozone containing gas from the ozone containing gas supply port to a treatment liquid in the treatment tank, a pulp fibers for saccharification formation step of forming the pulp fibers for saccharification from the pulp fibers while dissolving at least a portion of the super absorbent polymers in the treatment liquid, by, in the treatment tank, raising the ozone containing gas while lowering the super absorbent polymers and the pulp fibers so as to make the ozone containing gas come into contact with the super absorbent polymers and the pulp fibers, and a treatment liquid discharge step of discharging the treatment liquid which includes the pulp fibers for saccharification from the treatment liquid discharge port, wherein the pulp fibers for saccharification have a lignin content ratio of 0.1 mass % or less.

In used hygiene products, in absorbent bodies, etc., which include pulp fibers and super absorbent polymers, (i) as the super absorbent polymers absorb liquid, such as body fluid, etc., the super absorbent polymers enlarge and drag in the pulp fibers, and (ii) the enlarged super absorbent polymers cause gel blocking, etc., while dragging in the pulp fibers, whereby there are many cases in which a plurality of super absorbent polymers and a plurality of pulp fibers form a connected structure.

In the method described in Patent Literature 1, although the ozone containing gas treats the free pulp fibers which do not form the connected structure so as to decompose lignin which is included in the pulp fibers, since it is difficult for the ozone containing gas to come into contact with the pulp fibers which configure the connected structure, that is, the pulp fibers surrounded by the super absorbent polymers, there may be cases in which the pulp fibers which configure the connected structure cannot be sufficiently treated, that is, there may be cases in which it is difficult for the lignin which is included in the pulp fibers surrounded by the super absorbent polymers to be decomposed. Accordingly, the recycled pulp fibers which are manufacture by the method described in Patent Literature 1 include those with broad distribution of the lignin content ratio and high lignin content ratio. Further, in a case in which the used hygiene products that are to be the raw material include a plurality of types, for example, the same one type of products (disposable diapers for adults) sold by different companies, or different types of products (for example, disposable diapers for adults and disposable diapers for children) sold by the same company, the above-mentioned distribution of the lignin content ratio tends to be even broader. Incidentally, recycled pulp fibers with high lignin content ratio has a tendency that it is difficult for being saccharified.

The above-mentioned manufacturing method includes the predetermined pulp fibers for saccharification formation step, and in the pulp fibers for saccharification formation step, while lowering the super absorbent polymers and the pulp fibers, the ozone containing gas is raised, so as to make the super absorbent polymers and the pulp fibers come into contact with the ozone containing gas. Among the free super absorbent polymers, the free pulp fibers, and the connected structure, the free super absorbent polymers and the connected structure which have relatively higher specific gravity tend to have higher sedimentation than the free pulp fibers which have relatively lower specific gravity. On the other hand, since the ozone containing gas consumes ozone and rises while treating the super absorbent polymers and the pulp fibers, the ozone containing gas which is present in a lower position tends to have higher ozone content ratio (that is, being fresher) than the ozone containing gas which is present in an upper position.

Incidentally, in the present description, the lowering speed relates to the movement speed of the treatment liquid 52 in the treatment tank 31 toward the lower portion, and generally is uniquely determined by a first flow rate, a second flow rate, the size of the treatment tank, etc. On the other hand, in the present description, the sedimentation means the property of the pulp fibers, the super absorbent polymers and the connected structure which are included in the treatment liquid 52 in the treatment tank 31, expressing the ease of falling in the vertical direction due to gravity, and in accordance with the specific gravity, etc., each of the pulp fibers, the super absorbent polymers, and the connected structure has different sedimentations.

Accordingly, in the above-mentioned method, the free super absorbent polymers and the super absorbent polymers in the connected structure which have relatively high sedimentation are oxidatively decomposed by fresher ozone containing gas so as to free the pulp fibers which configure the connected structure, and further, the free pulp fibers which have relatively low sedimentation and taking relatively more time to reach the treatment liquid discharge port can be treated with more time by the ozone containing gas, so that the lignin included in the free pulp fibers can be decomposed.

Further, generally, since the pulp fibers have a tendency that the higher the lignin content ratio is, the higher the specific gravity is, in the above-mentioned method, the pulp fibers which have relatively higher lignin content ratio have relatively higher sedimentation than the pulp fibers which have relatively lower lignin content ratio, and thus fresher ozone containing gas comes into contact with the pulp fibers which have relatively higher lignin content ratio so as to decompose lignin included therein.

In the above-mentioned method, not only it is difficult for the pulp fibers for saccharification manufactured by the above-mentioned method to broaden the distribution of the lignin content ratio, but also the above-mentioned pulp fibers for saccharification includes the lignin content ratio with a predetermined low concentration. Accordingly, in the above-mentioned method, pulp fibers for saccharification that have low lignin content ratio and narrow distribution thereof, and have excellent saccharification property can be manufactured.

[Aspect 2]

The method according to aspect 1, wherein the pulp fibers for saccharification have a water contact angle of 20° or less.

When the hygiene products are recycled, it is easy for the oil content of the hot melt adhesive agent included in the hygiene products to be absorbed in the pulp fibers. Further, lignin included in the pulp fibers has a hydrophobic property.

In the method described in Patent literature 1, although the ozone in the ozone containing gas can oxidatively decompose the hydrophobic components such as the oil content of the pulp fibers which do not configure the connected structure, and lignin, etc., since it is difficult for the ozone in the ozone containing gas to come into contact with the pulp fibers which configure the connected structure, there may have been cases in which the hydrophobic components in the pulp fibers were not sufficiently oxidatively decomposed.

Accordingly, when the recycled pulp fibers which are manufactured by the method described in Patent literature 1 is used as the pulp fibers for saccharification, especially when the recycled pulp fibers are dried, it may be conceivable that it is difficult for the recycled pulp fibers to be dispersed in an aqueous solution for saccharification, or it takes time to be dispersed.

According to the above-mentioned manufacturing method, since the pulp fibers for saccharification which are manufactured by the above-mentioned manufacturing method have a predetermined water contact angle, the pulp fibers for saccharification which are manufactured by the above-mentioned manufacturing method can be dried and stored, and thereafter, can be easily dispersed in a saccharification aqueous solution. Accordingly, the above-mentioned manufacturing method can manufacture pulp fibers for saccharification which are excellent in saccharification property.

[Aspect 3]

The method according to aspect 1 or 2, wherein the pulp fibers for saccharification have a beating degree reduction speed of 300 mL/h or more.

According to the above-mentioned manufacturing method, since the pulp fibers for saccharification have a predetermined beating degree reduction speed, in the subsequent saccharification step, it is easy for the pulp fibers for saccharification to fluff when being applied with physical force, that is, to be increased in the surface area, whereby can be easily saccharified. Accordingly, the above-mentioned manufacturing method can manufacture pulp fibers for saccharification which are excellent in saccharification property.

[Aspect 4]

The method according to any one of aspects 1 to 3, wherein in the pulp fibers for saccharification formation step, the ozone containing gas is supplied from the ozone containing gas supply port as microbubbles or nanobubbles.

According to the above-mentioned manufacturing method, since ozone containing gas is supplied from the ozone containing gas supply port as microbubbles or nanobubbles, in the pulp fibers for saccharification formation step, even in a case in which the super absorbent polymers and the pulp fibers form a connected structure, the microbubbles or nanobubbles give buoyant force to the super absorbent polymers, the connected structure and the pulp fibers, whereby the sedimentations thereof decrease. Accordingly, it takes more time for the super absorbent polymers, the connected structure and the pulp fibers to reach the treatment liquid discharge port, so that ozone can decompose the free super absorbent polymers and the super absorbent polymers which configure the connected structure, and can sufficiently treat the free pulp fibers and the pulp fibers which configure the connected structure. Accordingly, the above-mentioned manufacturing method can manufacture pulp fibers for saccharification which are excellent in saccharification property.

[Aspect 5]

The method according to any one of aspects 1 to 4, wherein the treatment liquid is acidic.

According to the above-mentioned manufacturing method, the treatment liquid is acidic (for example, having pH of 2.5 or lower). Accordingly, in a case in which the super absorbent polymers to be treated can be inactivated by an acid or the super absorbent polymers to be treated are already inactivated, the super absorbent polymers can maintain the state of being inactivated. Thus, even in a case in which the super absorbent polymers and the pulp fibers form a connected structure, ozone in the ozone containing gas can remove the super absorbent polymers which configure the connected structure, and further, ozone in the ozone containing gas acts on the pulp fibers which configure the connected structure so as to reduce the lignin content ratio of the pulp fibers (form pulp fibers for saccharification which have low lignin content ratio).

Further, according to the above-mentioned manufacturing method, since the treatment liquid is acidic, it is easy for the treatment liquid which is to be discharged to be also acidic, whereby the discharged treatment liquid can be used in the saccharification step as it is, or after slight adjustment. This is because, in a case in which the saccharification step is performed, for example, under the presence of a cellulase enzyme, it is preferable that the saccharification step is performed not under an alkaline condition but under an acidic condition so as not to inhibit the activity of the cellulase enzyme.

[Aspect 6]

The method according to any one of aspects 1 to 5, further comprising an inactivation step of inactivating the super absorbent polymers by an acid, before the liquid mixture supply step.

Since the above-mentioned manufacturing method further includes a predetermined inactivation step, even in a case in which the super absorbent polymers and the pulp fibers form a connected structure, ozone in the ozone containing gas can remove the super absorbent polymers which configure the connected structure immediately after the liquid mixture which includes the super absorbent polymers that derive from used hygiene products, the pulp fibers and water, is supplied to the treatment tank, and further, ozone in the ozone containing gas acts on the pulp fibers which configure the connected structure so as to reduce the lignin content ratio of the pulp fibers (form pulp fibers for saccharification which have low lignin content ratio).

[Aspect 7]

The method according to aspect 6, wherein the acid is an acid which can form a complex with metal ions included in an excrement.

According to the above-mentioned manufacturing method, since the acid is an acid which can form a complex with metal ions included in an excrement, it is difficult for the pulp fibers for saccharification which are manufactured by the above-mentioned manufacturing method to include metal ions, whereby in a case in which the saccharification step is performed, for example, under the presence of a cellulase enzyme, it is difficult for the activity of the cellulase enzyme to be inhibited by metal ions.

[Aspect 8]

The method according to any one of aspects 1 to 7, wherein the pulp fibers for saccharification have an ash content ratio of 0.65 mass % or less.

According to the above-mentioned manufacturing method, since the pulp fibers for saccharification which are manufactured by the above-mentioned manufacturing method have a predetermined ash content ratio, in a case in which the saccharification step is performed, for example, under the presence of a cellulase enzyme, it is difficult for the activity of the cellulase enzyme to be inhibited by metal ions.

[Aspect 9]

The method according to any one of aspects 1 to 8, wherein in the liquid mixture supply step, the liquid mixture is supplied continuously from the liquid mixture supply port to the treatment tank in a first flow rate, and in the treatment liquid discharge step, the treatment liquid is discharged continuously from the treatment liquid discharge port in a second flow rate.

According to the above-mentioned manufacturing method, in the liquid mixture supply step, the liquid mixture is continuously supplied from the liquid mixture supply port to the treatment tank in the first flow rate, and in the treatment liquid discharge step, the treatment liquid is continuously discharged from the treatment liquid discharge port in the second flow rate, whereby the treatment time of the super absorbent polymers and the pulp fibers to be treated is equalized, the distribution of the lignin content ratio in the pulp fibers for saccharification is narrowed (with less variation), and as a result, in the saccharification step, the pulp fibers for saccharification can be efficiently saccharified.

[Aspect 10]

The method according to any one of aspects 1 to 9, further comprising a saccharification step of saccharifying the pulp fibers for saccharification, after the treatment liquid discharge step.

The above-mentioned manufacturing method can efficiently manufacture the saccharification solution from the pulp fibers for saccharification.

[Aspect 11]

An aqueous solution of pulp fibers for saccharification which derives from used hygiene products that include pulp fibers and super absorbent polymers, wherein the pulp fibers for saccharification have a lignin content ratio of 0.1 mass % or less.

According to the above-mentioned aqueous solution of pulp fibers for saccharification, the pulp fibers for saccharification have a predetermined lignin content ratio, whereby are excellent in saccharification property.

[Aspect 12]

The aqueous solution of pulp fibers for saccharification according to aspect 11, wherein the pulp fibers for saccharification have a beating degree reduction speed of 300 mL/h or more.

According to the above-mentioned aqueous solution of pulp fibers for saccharification, since the pulp fibers for saccharification have a predetermined beating degree reduction speed, in the subsequent saccharification step, it is easy for the pulp fibers for saccharification to fluff when being applied with physical force, that is, to be increased in the surface area, whereby can be easily saccharified.

[Aspect 13]

The aqueous solution of pulp fibers for saccharification according to aspect 11 or 12, wherein the aqueous solution of pulp fibers for saccharification is acidic.

Since the above-mentioned aqueous solution of pulp fibers for saccharification is acidic, in a case in which the saccharification step is performed, for example, under the presence of a cellulase enzyme, it is difficult for the activity of the cellulase enzyme to be inhibited.

[Aspect 14]

The aqueous solution of pulp fibers for saccharification according to aspect 13, wherein the aqueous solution of pulp fibers for saccharification includes an acid which can form a complex with metal ions included in an excrement.

Since the above-mentioned aqueous solution of pulp fibers for saccharification includes an acid which can form a complex with metal ions included in an excrement, in a case in which the saccharification step is performed, for example, under the presence of a cellulase enzyme, it is difficult for the activity of the cellulase enzyme to be inhibited by metal ions.

[Aspect 15]

The aqueous solution of pulp fibers for saccharification according to any one of aspects 11 to 14, wherein the pulp fibers for saccharification have an ash content ratio of 0.65 mass % or less.

According to the above-mentioned aqueous solution of pulp fibers for saccharification, since the pulp fibers for saccharification have a predetermined ash content ratio, in a case in which the saccharification step is performed, for example, under the presence of a cellulase enzyme, it is difficult for the activity of the cellulase enzyme to be inhibited by metal ions.

Hereinbelow, the method of manufacturing a saccharification solution from pulp fibers of used hygiene products (hereinbelow which may be simply referred to as "the manufacturing method of saccharification solution") is explained.

Incidentally, the used hygiene products are hygiene products which are used by users, include hygiene products in a state of having absorbed liquid excrement of users, and further include those which have been used but have not absorbed excrement, and those which have not yet been used, etc.

First, a configurational example of hygiene products is explained. A hygiene product includes a top sheet, a back sheet, and an absorbent body which is arranged between the top sheet and the back sheet. As the hygiene products, for example, a disposable diaper, a urine pad, a sanitary napkin, a bed sheet, a pet sheet, may be mentioned.

As the configurational material of the top sheet, for example, nonwoven fabric, or a film may be mentioned, and more specifically, liquid permeable nonwoven fabric, a synthetic resin film which has liquid permeation holes, and a composite sheet thereof, etc., may be mentioned. As the configurational material of the back sheet, for example, nonwoven fabric, or a film may be mentioned, and more specifically, liquid impermeable nonwoven fabric, a liquid impermeable synthetic resin film, and a composite sheet of such nonwoven fabric and synthetic resin film, may be mentioned.

As the configurational materials of the absorbent body, an absorbent core (for example, pulp fibers and super absorbent polymers), and a core wrap may be mentioned. As the pulp fibers, although not particularly limited as long as they can be used in hygiene products, and for example, cellulosic fibers may be mentioned. As the cellulosic fibers, for example, wood pulp, cross-linked pulp, non-wood pulp, regenerated, cellulose, semi-synthetic cellulose, etc., may be mentioned. As the super absorbent polymers (SAP), although not particularly limited as long as they can be used in hygiene products, and for example, those of polyacrylate based, polysulfonate based, and anhydrous maleate based, may be mentioned.

One surface and the other surface of the absorbent body are respectively joined to the top sheet and the back sheet through an adhesive agent. In a plan view, the portion which extends to the outer side of the absorbent body so as to surround the absorbent body (the peripheral portion) in the top sheet is joined to the portion which extends to the outer side of the absorbent body so as to surround the absorbent body (the peripheral portion) in the back sheet through an adhesive agent. Accordingly, the absorbent body is enclosed inside the joined body of the top sheet and the back sheet. As the adhesive agents, although not particularly limited as long as they can be used in hygiene products and the joining force thereof decreases due to softening with hot water, as described later, and for example, a hot melt adhesive agent may be mentioned. As the hot melt adhesive agent, for example, a pressure sensitive adhesive agent or heat sensitive adhesive agent made of rubber-based materials such as styrene-ethylene-butadiene-styrene, styrene-butadiene-styrene, styrene-isoprene-styrene, etc., or olefin-based materials such as polyethylene, etc., may be mentioned.

FIG. 1 is a flowchart which shows the material separation method of separating the used hygiene products into configurational materials. The material separation method is a method of separating the used hygiene products into films, nonwoven fabric, pulp fibers, and super absorbent polymers. The material separation method includes the pretreatment process S11, the disassembly process S12, and the separation process S13.

The pretreatment process S11 swells the used hygiene products with water. The disassembly process S12 applies physical force to the swollen used hygiene products so as to disassemble the used hygiene products into films, nonwoven fabric, and core wraps, etc., and the absorbent core (for example, the pulp fibers and the super absorbent polymers). The separation process S13 separates films, nonwoven fabric, the pulp fibers, and the super absorbent polymers from one another.

The manufacturing method of the saccharification solution according to the present disclosure is included in the separation process S13 among the material separation method. Incidentally, in a case in which the mixture of pulp fibers and super absorbent polymers is somehow obtained in advance, process prior to the manufacturing method of the saccharification solution in the pretreatment process S11, the disassembly process S12, and the separation process S13, need not be performed. Hereinbelow, each process is explained.

The pretreatment process S11 makes a plurality of used hygiene products absorb water so as to swell, in the same state as when recovered from outside, that is, in a state with no breaking or cutting, etc., and if being in a rolled state or a folded state, remaining as they are, and further, without inactivating the super absorbent polymers of the absorbent body. In the present embodiment, the used hygiene products are made to absorb hot water so as to swell, or the used hygiene products is made to absorb water so as to swell, and thereafter, the absorbed water is heated so as to be hot water. The hot water is referred to as water with higher temperature than a normal temperature (20° C.±15° C. (5 to 35° C.): JIS Z 8703).

Normally, the amount of liquid excrement which is actually absorbed in used hygiene products is extremely small compared to the maximum absorption amount which the hygiene products can absorb (for example, approximately 10 to 20 mass % of the maximum absorption amount). In the present embodiment, in pretreatment process S11, by immersing the used hygiene products in hot water, the used hygiene products are made to absorb water up to an amount close to the maximum absorption amount of the used hygiene products (for example, 80 mass % or more of the maximum absorption amount). Alternatively, the used hygiene products are immersed in water with a normal temperature, are made to absorb water up to an amount close to the maximum absorption amount of the used hygiene products, and thereafter, the entire used hygiene products are heated to a temperature of hot water. Accordingly, the used hygiene products can be brought to be in a state of being extremely swollen by hot water or water with a normal temperature (hereinbelow, which may simply be referred to as "hot water"). As a result, very high internal pressure is to be generated in the used hygiene products. Incidentally, the object of making water the hot water is mainly for weakening the adhesive force of the adhesive agent, as will be described later.

In a case in which the used hygiene products are initially in a state of being rolled or folded so that the back sheet is placed on the outer side (with the top sheet being hidden on the inner side), by being immersed in hot water, the absorbent bodies of the used hygiene products absorb hot water in hot water and swell. As a result, the internal pressure of the used hygiene products increases, the force to open toward the outer side is applied to the used hygiene products, whereby the used hygiene products which are in the rolled state of the folded state open toward the outer side so as to be almost in a flat state. That is, the used hygiene products can be made into a flat expanded state in the hot water. At this time, since the absorbent bodies have absorbed large amount of hot water and are extremely swollen, the used hygiene products are in a state in which it is easy for the surface thereof, that is, any of the portions of the top sheet and the back sheet which enclose the absorbent body to burst. That is, by the pretreatment process S11, the used hygiene products can be brought into a state in which either of the surfaces is about to be torn and cut. Incidentally, in a case in which the used hygiene products are initially in a state of being flat and expanded, either one of the surfaces is to easily burst as they are. Such a state cannot be brought in a case in which the used hygiene products have been broken, etc.

Further, by immersing the used hygiene products in hot water and/or making the used hygiene products absorb hot water, the adhesive agent (for example, a hot melt adhesive agent) used for joining each of the configurational materials can be softened by the heat of hot water, whereby the joining force of the adhesive agent can be decreased. For example, the adhesive agent which joins the peripheral portion of the top sheet and the peripheral portion of the back sheet can be softened by the heat of hot water, whereby the joining force of the adhesive agent can be decreased. Further, the adhesive agent which joins the top sheet and the absorbent body, and the adhesive agent which joins the back sheet and the absorbent body can be softened by the heat of hot water, whereby the joining force of the adhesive agents can be decreased.

In this manner, in the pretreatment process S11, by the swell of the absorbent bodies of the used hygiene products, the state in which any portion of the surfaces of the used hygiene products is to burst, and a state in which the joining force of the adhesive agent is decreased, can be brought. By the used hygiene products being brought into such a state, in the later-described disassembly process, the used hygiene products can be reliably disassembled.

The temperature of the hot water in the pretreatment process S11 is not particularly limited as long as the adhesive agent of the used hygiene products can be softened, and for example, 60° C. or higher may be mentioned, and preferably, the temperature is 70° C. or higher and 98° C. or lower. By setting the temperature of the hot water to 70° C. or higher, the adhesive agent used for joining each of the configurational materials can be softened by the heat of hot water, whereby the joining force of the adhesive agent can be decreased. By setting the temperature of the hot water to 98° C. or lower, the hot water is reliably present as liquid, whereby the used hygiene products can be reliably made to absorb hot water. By the swell of the absorbent bodies and the heat of hot water, the state of the surface of the used hygiene products being about to burst and the state in which the joining force of the adhesive agent is decreased are more reliably brought. The measurement of the temperature may be performed by measuring the temperature of hot water in which the used hygiene products are immersed, or measuring the portion on an inner side by 5 mm from the surface of the used hygiene products which have absorbed water up to an amount close to the maximum absorption amount (by inserting the tip of a temperature sensor).

Further, in reusing the used hygiene products, the sterilization of the configurational materials is very important. By setting the temperature of hot water to 70° C. or higher, it is preferable since the effect of sterilizing (disinfecting) the used hygiene products can be obtained.

The treatment time in the pretreatment process S11, that is, the time during which the used hygiene products are immersed in hot water, is not particularly limited as long as the absorbent bodies of the used hygiene products can swell, and for example, is 2 to 60 minutes, and is preferably 4 to 30 minutes. When the time is too short, the absorbent bodies cannot sufficiently swell, and when the time is too long, it will be a waste of time and the treatment cost increases unnecessarily.

Further, the absorption amount of hot water by the absorbent bodies in the pretreatment process S11 is not particularly limited as long as the absorbent bodies can swell to such an extent that the used hygiene products can be disassembled in the later-described disassembly process, and for example, is 80 mass % or more of the maximum absorption amount of the used hygiene products, and preferably is 90 mass % or more thereof. Accordingly, the used hygiene products can be brought into a state of being swollen with being inflated with water. As a result, an extremely high internal pressure can be generated in the absorbent bodies of the used hygiene products.

Note that the maximum absorption amount is measured in the following procedures.

(1) Unused hygiene products are subjected to drying treatment in an atmosphere of 100° C. or higher, and the mass of the hygiene products is measured.

(2) In a case in which elastic materials which are capable of forming pockets so that it is difficult for water to reach the absorbent bodies (for example, elastic members surrounding the leg circumferences, the waist circumferences, etc.) are arranged in the hygiene products, cuts are made in the elastic materials, whereby the hygiene products are flattened.

(3) The hygiene products are immersed in a water bath which is filled with sufficient amount of tap water with the top sheet facing downward, and are left for 30 minutes.

(4) After being left, the hygiene products are placed on a net with top sheet facing downward, and after 20 minutes of draining, the mass of the hygiene products is measured.

Then, the mass difference before and after the hygiene products are immersed in tap water is defined as the maximum absorption amount.

Subsequently, the disassembly process S12 gives physical impact on the plurality of used hygiene products which have been expanded and swollen by the pretreatment process S11, so as to disassemble the plurality of used hygiene products into films (the back sheets), nonwoven fabric (the top sheets), the core wraps, and further into the absorbent cores (for example, the absorbent bodies and the super absorbent polymers).

The used hygiene products are brought by the pretreatment process S11 to be expanded and flat, and portions of either of the surfaces are about to be torn by the swell, and in the present embodiment, especially by the heat of hot water, the used hygiene products are brought to be in a state in which the joining force of the adhesive agent is decreased. Accordingly, in the disassembly process S12, the used hygiene products in such a state are applied with physical impact, whereby among the portions of either of the surfaces, the joining portion of the top sheet (the nonwoven fabric) and the back sheet (the film) in which the joining force is especially decreased is torn off. Thus, the joining portion can be torn (peeled) off. As the physical impact, although not particularly limited, for example, a method of beating the used hygiene products on a surface which is made of a harder material than the used hygiene products, a method of, while sandwiching and letting the used hygiene products pass through a pair of rolls arranged so as to face each other, pressing the used hygiene products from both sides, etc., may be mentioned.

In the present embodiment, the disassembly process S12 includes a throwing process of throwing the plurality of swollen used hygiene products in a bottom portion of a rotation drum with a horizontal rotation axis, and a beating process of rotating the rotation drum around the rotation axis so as to repeat raising the plurality of used hygiene products to the upper portion of the rotation drum and beating the used hygiene products on the bottom portion. Accordingly, physical impact can be added to the plurality of used hygiene products stably, continuously and easily. As the rotation drum, for example, a rotation drum of a washing tub of a horizontal-type washing machine may be mentioned, and accordingly, the disassembly process S12 can be performed by using an existing horizontal-type washing machine (for example, ECO-22B, manufactured by Inax Corporation). As the size of the rotation drum, although not particularly limited as long as the above-mentioned impact can be realized, the inner diameter and depth may for example be 50 to 150 cm, and 30 to 120 cm, respectively. As the rotation speed of the rotation drum, although not particularly limited as long as the above-mentioned impact can be realized, for example, 30 times/minute to 100 times/minute, may be mentioned.

Further, although the temperature of the used hygiene products is maintained relatively high by the hot water absorbed inside the used hygiene products, from the viewpoint of suppressing the temperature drop of the adhesive agent, and maintaining the sterilization effect, the temperature of the atmosphere inside the rotation drum is preferably 70° C. or higher, and is more preferably 75° C. or higher. The temperature inside the rotation drum is, from the viewpoint of handling the used hygiene products, preferably 98° C. or lower, and is more preferably 90° C. or lower. It is preferable that the amount of water inside the rotation drum is as small as possible, and it is preferable that such amount is small to an extent that the used hygiene products would not be underneath the water surface at least in the bottom portion. When the used hygiene products are underneath the water surface, the impact on the used hygiene products is absorbed by water, whereby it is difficult to give a desired impact on the used hygiene products. The time during which the rotation drum is rotated is not particularly limited as long as the top sheets, the back sheets, and the core wraps, etc., and the absorbent cores can be disassembled, and for example, 2 to 40 minutes may be mentioned, and is preferably 4 to 20 minutes.

The joining portion of the top sheets (the nonwoven fabric) and the back sheets (the films) of the used hygiene products is busted and torn off by the physical impact. At the same time, through the gash, the absorbent core (for example, the pulp fibers and the super absorbent polymers) inside the used hygiene products erupts (pops out), by the internal pressure of the absorbent bodies. Accordingly, the used hygiene products can be more reliably disassembled into the top sheets (the nonwoven fabric), the back sheet (the films), the core wraps, etc., and into the absorbent cores (for example, the pulp fibers and the super absorbent polymers).

Subsequently, the separation process S13 separates the plurality of films (the back sheets), the plurality of pieces of nonwoven fabric (the top sheets), the core wraps, etc., and the absorbent cores (for example, the pulp fibers and the super absorbent polymers), from one another. Note that the nonwoven fabric may be kept joined to the films. As the above-mentioned separation method, although not particularly limited, for example, a method of using a sieve which does not let the top sheets, the back sheets, and the core wraps, etc., pass through and lets the absorbent cores pass through, may be mentioned.

In the present embodiment, the separation process S13 may include, before separating the films, the nonwoven fabric, the core wraps, etc., and the absorbent core, from one another, the inactivation process S31 of inactivating the super absorbent polymers by an aqueous solution including an inactivation agent, and the first separation process S32 of separating the films and the nonwoven fabric; and the mixture of the pulp fibers, the inactivated super absorbent polymers, and waste water which is discharged from the super absorbent polymers by the inactivation; from one another.

In the inactivation process S31, before the first separation process S32, the top sheets (the nonwoven fabric), the back sheets (the films), and the absorbent bodies (the pulp fibers and the super absorbent polymers) are immersed in an aqueous solution including an inactivation agent which is capable of inactivating the super absorbent polymers. Accordingly, the super absorbent polymers which have been attached to the top sheets, the back sheets, and the pulp fibers can be inactivated. Thus, the super absorbent polymers in a state of high viscosity before the inactivation can be brought into super absorbent polymers in a state of low viscosity, by dehydration caused by the inactivation.

As the inactivation agent, although not particularly limited, acid (for example, an inorganic acid and an organic acid), lime, calcium chloride, magnesium sulfate, magnesium chloride, aluminum sulfate, aluminum chloride, etc., may be mentioned. The above-mentioned acid is preferable since acid does not let ash be left in the pulp fibers. In a case in which acid is used as the inactivation agent, pH thereof is preferably 2.5 or lower, and is more preferably 1.3 to 2.4. When the pH thereof is too high, the absorption ability of the super absorbent polymers cannot be sufficiently reduced. Further, there is also a possibility that the sterilization ability may be reduced. When the pH thereof is too low, there is a risk that the equipment may be corroded, and many alkaline chemicals are to be required for neutralization treatment during water discharged treatment.

As the above-mentioned inorganic acid, for example, sulfuric acid, hydrochloric acid, and nitric acid may be mentioned, although sulfuric acid is preferable from the viewpoint of not including chlorine and of cost, etc. On the other hand, as the above-mentioned organic acid, citric acid, tartaric acid, glycolic acid, malic acid, succinic acid, acetic acid, ascorbic acid, etc., may be mentioned, although hydroxyl carbonate based organic acid such as citric acid, tartaric acid, gluconic acid, etc., which can form a complex with metal ions included in an excrement is especially preferable. Incidentally, as the metal ions included in an excrement, calcium ions may be mentioned. This is because, by the chelating effect of the acid which can form a complex with metal ions included in an excrement, the metal ions in an excrement are trapped and can be removed. Further, citric acid has a cleaning effect, whereby a high waste component removal effect can be expected.

Incidentally, since pH changes depending on water temperature, pH in the present disclosure is the one measured at the temperature of 20° C. of an aqueous solution.

The treatment temperature of the inactivation process S31, that is, the temperature of the aqueous solution including the inactivation agent, is not particularly limited as long as the reaction of the inactivation proceeds. The treatment temperature may be room temperature, or may be higher than the room temperature, and for example, 15 to 30° C. may be mentioned. Further, the treatment time of the inactivation process S31, that is, the time during which the top sheets, the back sheets and the absorbent bodies are immersed in the aqueous solution including the inactivation agent, is not particularly limited as long as the super absorbent polymers are inactivated and are dehydrated, and for example, 2 to 60 minutes may be mentioned, and preferably is 5 to 30 minutes. Still further, the amount of the aqueous solution in the inactivation process S31, that is, the amount of the aqueous solution including the inactivation agent is not particularly limited as long as the reaction of the inactivation proceeds. The amount of the aqueous solution may be, for example, with respect to 100 parts by mass of the used hygiene products, preferably 300 to 3000 parts by mass, more preferably 500 to 2500 parts by mass, and even more preferably 1000 to 2000 parts by mass.

In the first separation process S32, the top sheets (the nonwoven fabric), the back sheets (the films), the core wraps; and the mixture of the pulp fibers, the inactivated super absorbent polymers, and waste water which is discharged from the super absorbent polymers by the inactivation; are separated from one another. Note that the waste water is the moisture released from the super absorbent polymers by the dehydration of the aqueous solution including the inactivation agent in the inactivation process S31, that is, the waste water including body fluid derived from an excrement and water derived from the hot water.

In the first separation process S32, the method of separating the top sheets, the back sheets, the pulp fibers, the super absorbent polymers and the waste water from one another is not particularly limited. For example, the products produced by the inactivation process (the top sheets, the back sheets, the pulp fibers, the super absorbent polymers and the waste water) may be discharged while being let to pass through a screen with openings of 5 to 100 mm, and preferably of 10 to 60 mm. Accordingly, the pulp fibers, the super absorbent polymers and the waste water are brought into the discharged water, while the top sheets and the back sheets remain on the screen, whereby such products can be separated. Incidentally, large shaped materials of other nonwoven fabric, films, etc. may remain on the screen. Especially, before the inactivation, since the super absorbent polymers are in a state with high viscosity, it cannot be said that it is easy to separate the super absorbent polymers attached to the top sheets, the back sheets and the pulp fibers. However, after the inactivation, since the super absorbent polymers are brought to a state with low viscosity by the dehydration, the super absorbent polymers attached to the top sheets, the back sheets and the pulp fibers can be easily separated from the top sheets, the back sheets and the pulp fibers. Accordingly, the configurational materials of the hygiene products can be efficiently separated and recovered.

In the present embodiment, the separation process S13 may further include the second separation process S33 of, by a solvent which dissolves the adhesive agent in the joining portions of films and other materials, removing the adhesive agent in the joining portions. In the present embodiment, by a solvent which dissolves the adhesive agent in each of the joining portions of the films, the nonwoven fabric, and the absorbent bodies, the adhesive agent in each of the joining portions is removed.

In the second separation process S33, the adhesive agent in the joining portions of the films (the back sheets) and other materials (the nonwoven fabric of the top sheets, the absorbent bodies remaining on the surfaces of the top sheets and the back sheets, etc.) is removed by a solvent. Accordingly, the films and the other materials can be separated from each other without breaking them and as they are. Thus, the configurational materials such as the films of the hygiene products can be efficiently recovered. Further, since the films and the other materials can be separated from each other without remaining the adhesive agent on the films, the films can be brought to be reusable as resin with high purity. Accordingly, adverse effects caused by the adhesive can be suppressed when reusing the films. The same can be said for the nonwoven fabric.

As the solvent to be used in the second separation process S33, although not particularly limited as long as it can dissolve the adhesive agent, for example, terpenes including at least one of terpene hydrocarbons, terpene aldehydes, and terpene ketones, may be mentioned. In this process, an aqueous solution including terpene is used, and the concentration of terpene in the aqueous solution is for example, 0.05 mass % or higher and 2 mass % or lower. Preferably, the concentration is 0.075 to 1 mass %. When the concentration of terpenes is too low, there is a possibility that the adhesive agent in the joining portion may not be dissolved. When the concentration of terpenes is too high, the cost may be too expensive. Further, not only does terpene dissolve an adhesive agent such as a hot melt adhesive agent, but also terpene has oil stain cleaning effect. Accordingly, when printing is provided in the configurational materials of the hygiene products, such as the back sheets, etc., terpene can also decompose and remove the printing ink.

As the terpene hydrocarbons, for example, myrcene, limonene, pinene, camphor, sapinene, ferrandlene, paracymene, osymene, terpinene, karen, zingiberene, caryophyllene, bisabolene, cedrene, may be mentioned. Among these, limonene, pinene, terpinene, karen are preferable. Further, as the terpene aldehydes, for example, citronellal, citral, cyclocitral, safranal, ferrandral, perilaldehyde, geranial, neral, may be mentioned. As the terpene ketones, for example, camphor, thujone, may be mentioned. Among the terpenes, the terpene hydrocarbons are preferable, and limonene is especially preferable. There are three types of limonene: d-limonene, l-limonene, dipentene (dl-limonene), and all of these types can be preferably used. The terpenes can be used singly of one type, or can be used by combining two or more types thereof.

The treatment temperature of the second separation process S33, that is the temperature of the aqueous solution including the solvent, is not particularly limited as long as the dissolving of the adhesive agent proceeds and the configurational materials of the used hygiene products are disassembled. The treatment temperature may be room temperature, or may be higher than the room temperature, and for example, 15 to 30° C. may be mentioned. Further, the treatment time of the second separation process S33, that is, the time during which the top sheets, the back sheets and the absorbent bodies are immersed in the aqueous solution including the solvent, is not particularly limited as long as the dissolving of the adhesive agent proceeds and the configurational materials of the used hygiene products are disassembled. As the treatment time, for example, 2 to 60 minutes may be mentioned, and preferably the treatment time is 5 to 30 minutes. Still further, the amount of the aqueous solution in the second separation process S33, that is, the amount of the aqueous solution including the solvent, is not particularly limited as long as the dissolving of the adhesive agent proceeds and the configurational materials of the used hygiene products are disassembled. The amount of the aqueous solution may be, for example, with respect to 100 parts by mass of the used hygiene products, preferably 300 to 3000 parts by mass, and more preferably 500 to 2500 parts by mass. By the second separation process S33, the amount of the adhesive agent which remains in the films, the nonwoven fabric, the absorbent bodies, etc., can be brought to be 1 mass % or lower with respect to the films, the nonwoven fabric, the absorbent bodies, etc.

Incidentally, in the present embodiment, as another preferable aspect, the above-mentioned second separation process S33 can be also performed in the above-mentioned inactivation process S31. That is, while inactivating the super absorbent polymers which are attached to the top sheets, the back sheets and the pulp fibers, the adhesive agent which is attached to the top sheets, the back sheets and the pulp fibers may be dissolved. In this case, as the aqueous solution in which the top sheets, the back sheets, the pulp fibers, and the super absorbent polymers are immersed, an aqueous solution which includes both of the inactivation agent and a solvent is used. Accordingly, in the above-mentioned inactivation process S31, the back sheets (the films), the top sheets (the nonwoven fabric), and the absorbent bodies (the pulp fibers and the super absorbent polymers) can brought to be in a state of being generally separated in the aqueous solution. Then, in the subsequent first separation process, the back sheets (the films), the top sheets (the nonwoven fabric), the absorbent bodies (the pulp fibers and the super absorbent polymers) can be separated from one another, and the second separation process S33 can be omitted. In this case, the back sheets (the films) and the top sheets (the nonwoven fabric) are substantially separated from each other by the removal of the adhesive agent.

In the present embodiment, the separation process S13 may further include the first drying process S34, subsequent to the process of removing the adhesive agent in the joining portion, of drying the films in an atmosphere with a temperature higher than the room temperature or by hot air so as to remove the solvent. In the present embodiment, the nonwoven fabric is also dried in this process.

In reusing used hygiene products, the sterilization is very important. In the first drying process S34, the process of drying the separated films (the back sheets) and the nonwoven fabric (the top sheets) in an atmosphere with a high temperature or by hot air is performed. The drying temperature is, for example, 105 to 210° C., and is preferably 110 to 190° C. The drying time is, although depending on the drying temperature, for example, 10 to 120 minutes, and is preferably 15 to 100 minutes. Accordingly, not only the solvent which remains on the surfaces of the films and the nonwoven fabric is evaporated and removed, but also the films and the nonwoven fabric can be sterilized by the atmosphere with a high temperature or hot air, etc. Thus, it becomes possible to exhibit an effect of the sterilization (the disinfection) while removing the solvent.

On the other hand, in the present embodiment, the separation process S13 may include the third separation process S35 of separating the pulp fibers from the separated mixture. In the third separation process S35, the method of separating the pulp fibers from the separated mixture (which includes the pulp fibers, the super absorbent polymers, and the waste water) is not particularly limited, and for example, the separated mixture is discharged while being let to pass through a screen with openings of 0.1 to 4 mm, and preferably of 0.15 to 2 mm. Accordingly, the super absorbent polymers and the waste water are brought into the discharged water, while the pulp fibers (in which the super absorbent polymers remain mainly on the surface thereof) remain on the screen, whereby the pulp fibers can be separated from the mixture. Although such pulp fibers include a large amount of impurities, the pulp fibers can be reused in this state depending on the application.

In the separated pulp fibers, the super absorbent polymers are attached, and the separated pulp fibers and the super absorbent polymers attached to the pulp fibers are mixed with water by a predetermined ratio, whereby proceed to the ozone treatment process S36 as a liquid mixture.

In the present embodiment, the separation process S13 includes the ozone treatment process S36 of treating the liquid mixture which includes the super absorbent polymers and the pulp fibers, the connected structure thereof, and water, by an aqueous solution including ozone, whereby lowers the molecular weight of the super absorbent polymers attached to the pulp fibers, and solubilizes and removes the same.

In used hygiene products, in absorbent bodies, etc., which include pulp fibers and super absorbent polymers, (i) as the super absorbent polymers absorb liquid, such as body fluid, etc., the super absorbent polymers enlarge and drag in the pulp fibers, and (ii) the enlarged super absorbent polymers cause gel blocking, etc., while dragging in the pulp fibers, whereby there are many cases in which a plurality of super absorbent polymers and a plurality of pulp fibers form a connected structure. In the above-mentioned liquid mixture, in addition to the free pulp fibers and the free super absorbent polymers, the connected structure which is configured by a plurality of super absorbent polymers and a plurality of pulp fibers is included.

In the ozone treatment process S36, the super absorbent polymers which are included in the liquid mixture (the treatment liquid) are oxidatively decomposed by ozone in the aqueous solution so as to be solubilized in the aqueous solution, whereby are removed.

The state in which the super absorbent polymers are oxidatively decomposed and are solubilized in an aqueous solution is a state in which the super absorbent polymers and the connected structure pass through a screen with openings of 2 mm. Accordingly, the impurities such as the super absorbent polymers, etc., can be removed from the liquid mixture (the treatment liquid) and the pulp fibers with high purity can be generated. Further, by the ozone treatment, the secondary sterilization, the bleach, and the deodorization of the pulp fibers can be performed.

Figure 2:
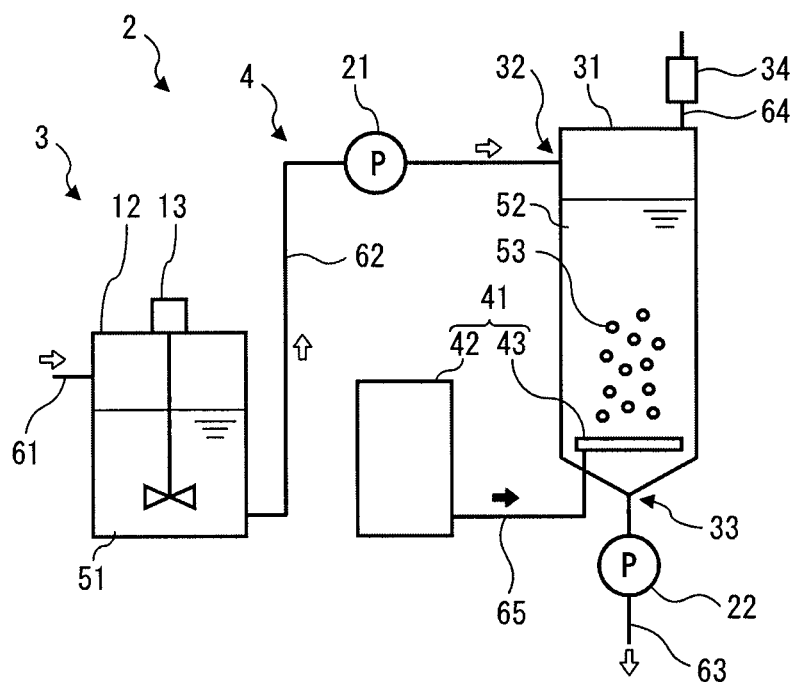
FIG. 2 is a schematic view which shows a configurational example of an apparatus of the ozone treatment process of FIG. 1.

FIG. 2 is a schematic view which shows one example of the configuration of the apparatus 2 that performs the ozone treatment process S36. The apparatus 2 includes the liquid mixture storage portion 3 which stores the liquid mixture 51 that includes water, the pulp fibers and the super absorbent polymers which have been separated in the third separation process S35, and the ozone treatment portion 4 which oxidatively decomposes the super absorbent polymers included in the liquid mixture 51 so as to remove the same from the pulp fibers.

The liquid mixture storage portion 3 includes the liquid mixture tank 12 and the stirring machine 13. The liquid mixture tank 12 stores the liquid mixture 51 which is supplied through the pipe 61. The stirring machine 13 stirs the liquid mixture 51 in the liquid mixture tank 12 so that the pulp fibers and the super absorbent polymers in the liquid mixture 51 are not separated from water and do not sink downward in the liquid mixture 51.

On the other hand, the ozone treatment portion 4 includes the supply pump 21, the treatment tank 31, the ozone supply apparatus 41, the delivery pump 22, and the ozone decomposition apparatus 34. The treatment tank 31 includes an acidic aqueous solution as the treatment liquid 52. The treatment tank 31 includes the liquid mixture supply port 32, the treatment liquid discharge port 33, and the ozone containing gas supply port 43. The liquid mixture supply port 32 is arranged on the upper portion of the treatment tank 31, and supplies the liquid mixture 51 to the treatment tank 31. The treatment liquid discharge port 33 is arranged on the lower portion of the treatment tank 31, and discharges the treatment liquid 52. The ozone containing gas supply port 43 is arranged on the lower portion of the treatment tank 31, and more specifically is arranged on the upper portion compared to the treatment liquid discharge port 33, and delivers the ozone containing gas 53 into the treatment tank 31.

More specifically, the supply pump 21 supplies continuously the liquid mixture 51 in the liquid mixture tank 12 through the pipe 62 from the liquid mixture supply port 32 into the treatment tank 31 in the first flow rate. The ozone supply apparatus 41 supplies the ozone containing gas 53 into the treatment tank 31. As the ozone generation apparatus 42 of the ozone supply apparatus 41, for example, the ozone water exposure tester ED-OWX-2 manufactured by EcoDesign, Inc., the ozone generation apparatus OS-25V manufactured by Mitsubishi Electric Corporation, etc., may be mentioned. The ozone containing gas 53 is a gas of different types of gas including ozone, and for example, an oxygen gas including ozone may be mentioned. The ozone containing gas supply port 43 delivers the ozone containing gas 53 which is supplied to the treatment tank 31 through the pipe 65 into the treatment tank 31, and is arranged on the lower portion (preferably at the bottom portion) of the treatment tank 31. The ozone containing gas supply port 43 supplies continuously the ozone containing gas 53 into the treatment liquid 52 from the lower portion toward the upper portion of the treatment liquid 52 (the treatment tank 31) as a plurality of fine bubbles. The delivery pump 22 discharges continuously the treatment liquid 52 inside the treatment tank 31 through the pipe 63 from the treatment liquid discharge port 33 to the outside of the treatment tank 31 in the second flow rate. The ozone decomposition apparatus 34 receives the ozone containing gas 53 which is accumulated at the upper portion of the treatment tank 31 through the pipe 64, detoxifies the ozone and releases the detoxified ozone to the outside. Incidentally, the treatment liquid 52 inside the treatment tank 31 is only the treatment liquid 52 before the initiation of the ozone treatment process S36, and after the initiation thereof, is to be the liquid in which the treatment liquid 52 and the liquid mixture 51 are mixed, however, in the present embodiment, the liquid inside the treatment tank 31 including the liquid in which the treatment liquid 52 and the liquid mixture 51 are mixed is altogether regarded as the treatment liquid 52.

Subsequently, the specific method of the ozone treatment process S36 is explained.

The pulp fibers and the super absorbent polymers which have been separated in the third separation process S35 are mixed with water so as to have a previously set concentration, whereby is to be the liquid mixture 51. The concentration of the pulp fibers in the liquid mixture 51 is set so as to have a previously set concentration in a state in which the pulp fibers are thrown into the treatment tank 31 and are mixed with the treatment liquid 52. The liquid mixture 51 is supplied to the liquid mixture tank 12 through the pipe 61, and is stored therein. Since the specific gravity of the pulp fibers and the super absorbent polymers is larger than 1, the liquid mixture 51 is stirred inside the liquid mixture tank 12 by the stirring machine 13 so that the pulp fibers and the super absorbent polymers do not separate with water.

Further, the liquid mixture 51 inside the liquid mixture tank 12 is controlled with the flow rate by the supply pump 21, and is supplied continuously through the pipe 62 from the liquid mixture supply port 32 to the treatment tank 31 in the first flow rate. The treatment liquid 52 is an acidic aqueous solution, and the specific gravity thereof is approximately 1. Accordingly, the pulp fibers and the super absorbent polymers sink from the upper portion to the lower portion of the treatment liquid 52.

On the other hand, the ozone containing gas 53 which is generated by the ozone generation apparatus 42 is supplied to the treatment tank 31 through the pipe 65, and is released from the ozone containing gas supply port 43 of the treatment tank 31 into the treatment liquid 52 in a state of fine bubbles (for example, as microbubbles or nanobubbles). That is, the ozone containing gas 53 rise from the lower portion toward the upper portion of the treatment liquid 52.

Further, the pulp fibers and the super absorbent polymers which move inside the treatment liquid 52 toward the lower portion, that is, which are lowered, and the ozone containing gas 53 which moves toward above, that is which rises, collide with each other while proceeding with facing each other. Further, the ozone containing gas 53 is attached to the surfaces of the pulp fibers, the super absorbent polymers, and the connected structure. The ozone in the ozone containing gas 53 oxidatively decomposes the free super absorbent polymers, and dissolves the same in the treatment liquid 52. Accordingly, the super absorbent polymers on the pulp fibers are removed from the pulp fibers. Further, the pulp fibers are lowered toward the bottom portion of the treatment tank 31, and the ozone containing gas 53 exits to the space in the upper portion of the treatment tank 31.

Among the free super absorbent polymers, the free pulp fibers, and the connected structure, the free super absorbent polymers and the connected structure including the super absorbent polymers which have relatively higher specific gravity tend to have higher sedimentation than the free pulp fibers which have relatively lower specific gravity. On the other hand, since the ozone containing gas consumes ozone and rises while treating the super absorbent polymers and the pulp fibers, the ozone containing gas which is present in a lower position tends to have higher ozone content ratio (that is, being fresher) than the ozone containing gas which is present in an upper position.

Accordingly, the free super absorbent polymers and the connected structure, the movement toward the lower position of which is relatively fast, can be properly oxidatively decomposed by a fresher ozone containing gas, whereby free pulp fibers can be formed. On the other hand, since the movement toward the lower position of the free pulp fibers is relatively slow, the ozone containing gas can treat the free pulp fibers (and the pulp fibers for saccharification to be formed) by taking time. To be more specific, ozone in the ozone containing gas collides with the pulp fibers while facing the same, whereby lignin of the pulp fibers (and the pulp fibers for saccharification) can be decomposed.

Subsequently, the treatment liquid 52 (including the pulp fibers for saccharification) in the bottom portion of the treatment tank 31 is discharged continuously from the treatment liquid discharge port 33 of the treatment tank 31 to the outside of the treatment tank 31 in the second flow rate through the pipe 63 by the flow rate control of the delivery pump 22. The ozone in the ozone containing gas 53 which is accumulated at the upper portion of the treatment tank 31 is detoxified by the ozone decomposition apparatus 34, and is released to the outside.

In this manner, the liquid mixture 51 is supplied continuously from the upper portion of the treatment tank 31 into the treatment tank 31 in the first flow rate, and the treatment liquid 52 is discharged continuously from the lower portion (the bottom portion) of the treatment tank 31 to the outside of the treatment tank 31 in the second flow rate. Accordingly, a continuous and stable flow of fluid (including the pulp fibers) from the upper portion toward the lower portion inside the treatment tank 31 can be forcibly caused.

The treatment liquid 52 which is to be discharged from the treatment tank 31 includes the pulp fibers for saccharification from which the super absorbent polymers are removed, and further includes organic matter with low molecular weight which is generated by the super absorbent polymers being oxidatively decomposed. The pulp fibers for saccharification is recovered in the process which is further downstream of the delivery pump 22, for example, in the fourth separation process S37 which will be described later.

The present method at least, while supplying continuously the liquid mixture 51 which includes the pulp fibers and the super absorbent polymers into the treatment tank 31 which includes the treatment liquid 52 capable of dissolving the super absorbent polymers in the first flow rate, discharges continuously the treatment liquid 52 which includes the pulp fibers for saccharification from which the super absorbent polymers are removed, and further includes organic matter with low molecular weight which is generated by the super absorbent polymers being oxidatively decomposed, to the outside of the treatment tank 31 in the second flow rate. By having such a configuration, a continuous and stable flow of fluid (including the pulp fibers) from the liquid mixture supply port 32 which supplies the liquid mixture 51 in the treatment tank 31 toward the treatment liquid discharge port 33 which discharges the treatment liquid 52 can be forcibly caused. By the flow of fluid, that is, by the water stream, even when the treatment amount of the pulp fibers and the super absorbent polymers is increased, the super absorbent polymers can be treated (solubilized) and the pulp fibers can be treated.

The first flow rate and the second flow rate are preferably the same. By setting the first flow rate and the second flow rate the same, the amount of the treatment liquid 52 inside the treatment tank 31 can be maintained constant, and the treatment can be performed stably and continuously. Note that when the amount of the treatment liquid 52 inside the treatment tank 31 can be maintained approximately constant, that is, if the amount of the treatment liquid 52 inside the treatment tank 31 does not largely increase or decrease, the first flow rate and the second flow rate may vary over time. That is, the first flow rate and the second flow rate do not necessarily have to be completely the same at all times, and may be approximately the same on average over time. Note that "approximately the same" is referred to as the difference between the first flow rate and the second flow rate being within 5 mass % or less. Also in such a case, the treatment can be performed stably and continuously.

In a case in which the ozone containing gas 53 is supplied to the treatment liquid 52, the ozone concentration in the treatment liquid 52 is not particularly limited as long as the ozone can oxidatively decompose the super absorbent polymers, and for example, 1 to 50 mass ppm may be mentioned, and the ozone concentration is preferably 2 to 40 mass ppm, and more preferably 3 to 30 mass ppm. When the ozone concentration in the treatment liquid 52 is too low, the super absorbent polymers may not be completely solubilized, and the super absorbent polymers may remain in the pulp fibers. Conversely, when the ozone concentration in the treatment liquid 52 is too high, since the oxidizing power also increases, the pulp fibers may be damaged, and further, it is possible that safety issues may be caused. The ozone treatment temperature is not particularly limited as long as the super absorbent polymers can be oxidatively decomposed, and for example, the temperature may be kept in room temperature, or may be set to a temperature higher than the room temperature.

The concentration of ozone in the treatment liquid 52 (the aqueous solution) is measured by the following method.

(1) In a 100 mL graduated cylinder containing approximately 0.15 g of potassium iodide and 5 ml of 10% citric acid solution, 85 mL of the treatment liquid 52 in which ozone is dissolved is added and reacted.

(2) The treatment liquid 52 after reaction is moved to 200 mL Erlenmeyer flask, a starch solution is added to the Erlenmeyer flask, and is colored to purple, and thereafter, titration is performed while stirring the mixture until the mixture become colorless by 0.01 mol/L of sodium thiosulfate, and the addition amount a (mL) is recorded.

(3) The concentration of ozone in the aqueous solution is calculated by using the following formula.

The concentration of ozone in the aqueous solution (mass ppm) is calculated by the following formula:

$$\text{The concentration of ozone in the aqueous solution (mass ppm)} = a \text{ (mL)} \times 0.24 \times 0.85 \text{ (mL)}$$

The ozone concentration in the ozone containing gas 53 is preferably 40 to 200 $g/m^3$, more preferably 40 to 150 $g/m^3$, and even more preferably 40 to 100 $g/m^3$. When the ozone concentration in the ozone containing gas 53 is too low, the super absorbent polymers may not be completely solubilized, and the super absorbent polymers may remain. When the ozone concentration in the ozone containing gas 53 is too high, the pulp fibers may be damaged, safety may be reduced, and the manufacturing costs may increase. Incidentally, the ozone concentration in the ozone containing gas 53 may be measured, for example, by a UV absorption type ozone concentration meter (for example, ozone monitor OZM-5000G manufactured by EcoDesign, Inc.).

The concentration of the pulp fibers and the super absorbent polymers in the treatment liquid 52 is not particularly limited as long as the super absorbent polymers can be oxidatively decomposed by the ozone in the treatment liquid 52, and for example, 0.1 to 20 mass % may be mentioned, and the concentration thereof is preferably 0.2 to 10 mass %, and is more preferably 0.3 to 5 mass %. When the concentration of the pulp fibers is too high, the super absorbent polymers may not be completely solubilized, and the super absorbent polymers may remain in the pulp fibers. Conversely, when the concentration of the pulp fibers is too low, since the oxidizing power also increases, the pulp fibers may be damaged, and further, it is possible that safety issues may be caused. The concentration of the pulp fibers and the super absorbent polymers in the liquid mixture 51 is appropriately set based on the above-mentioned concentration of the pulp fibers and the super absorbent polymers in the treatment liquid 52 and the amount of the treatment liquid 52.

In a case in which ozone is supplied to the treatment liquid 52 which includes the pulp fibers and the super absorbent polymers, the treatment liquid 52 is preferably acidic. More preferably, pH of the treatment liquid 52 is higher than 0 and is 5.0 or lower, and even more preferably, is 1.5 to 2.5. By being treated in an acidic state, the inactivation of ozone is suppressed, the oxidative decomposition effect for the super absorbent polymers by ozone is improved, whereby the super absorbent polymers can be oxidatively decomposed in a short amount of time. In order to maintain pH of the treatment liquid, pH of the liquid mixture 51 may be set to the same as that of the treatment liquid 52, and the liquid mixture 51 may be supplied to the treatment tank 31. Alternatively, pH of the treatment liquid 52 may be monitored by a pH sensor, and when pH is varied to the neutral side, a predetermined acidic aqueous solution may be added to the treatment liquid 52 by the amount in accordance with the varied range.

The amount of the treatment liquid 52 (including the liquid mixture 51) inside the treatment tank 31 is not particularly limited as long as it can oxidatively decompose the super absorbent polymers, although it is preferable that the volume V (unit: L) of the treatment liquid 52 inside the treatment tank 31 and the mass W (unit: kg) of the pulp fibers satisfy $30 \leq V/W \leq 1000$. It is more preferable that they satisfy $50 \leq V/W \leq 400$, and even more preferable that they satisfy $100 \leq V/W \leq 200$. When V/W is too small, the super absorbent polymers may not be completely solubilized, and the super absorbent polymers may remain. When V/W is too large, the manufacturing costs may increase. Incidentally, the volume V of the treatment tank 31 is not particularly limited, and for example, 50 to 80 L may be mentioned.

It is preferable that the flow rate $R_O$ (unit: L/minute) of the ozone containing gas and the volume V (unit: L) of the treatment liquid 52 inside the treatment tank 31 satisfy $0.01 \leq R_O/V \leq 1.25$. It is more preferable that they satisfy $0.03 \leq R_O/V \leq 1.0$, and even more preferable that they satisfy $0.06 \leq R_O/V \leq 0.75$. When $R_O/V$ is too small, the super absorbent polymers may not be completely solubilized, and the super absorbent polymers may remain in the pulp fibers. When $R_O/V$ is too large, the pulp fibers may be damaged, safety may be reduced, and the manufacturing costs may increase. Incidentally, the flow rate $R_O$ of the ozone containing gas is not particularly limited, and for example, 3 to 6 L/minute may be mentioned.

The time during which the pulp fibers are present inside the treatment tank 31, that is, the time during which the pulp fibers are treated in the treatment liquid 52 (hereinbelow, which may also be referred to as "the in-tank treatment time") is not particularly limited as long as such time can oxidatively decompose the super absorbent polymers. The in-tank treatment time may be short when the ozone concentration of the treatment liquid 52 is high, and it takes a long time when the ozone concentration of the treatment liquid 52 is low. As the in-tank treatment time, for example, 2 to 60 minutes may be mentioned, and the in-tank treatment time is preferably 5 to 30 minutes. The product (hereinbelow, which may also be referred to as "the CT value") of ozone concentration (mass ppm) in the treatment liquid 52 and the in-tank treatment time (minute) is preferably 100 to 6000 ppm·minute, is more preferably 200 to 4000 ppm·minute, and is even more preferably 300 to 2000 ppm·minute. When the CT value is too small, the super absorbent polymers may not be completely solubilized, and the super absorbent polymers may remain in the recovered pulp fibers. When the CT value is too large, the pulp fibers may be damaged, safety may be reduced, and the manufacturing costs may increase.

While the pulp fibers are present inside the treatment tank 31, the super absorbent polymers are oxidatively decomposed into components with low molecular weight by ozone, and are dissolved in the treatment liquid 52. The components with low molecular weight which are dissolved in the treatment liquid 52 are discharged together with the treatment liquid 52. Further, in this process, by the sterilization action of ozone, the used hygiene products are subjected to primary disinfection.

In the present embodiment, as a preferred aspect, the ozone treatment process S36 (the continuous treatment process) includes the process of while supplying continuously the liquid mixture 51 from the upper portion of the treatment tank 31, discharging continuously the treatment liquid 52 from the lower portion of the treatment tank 31. Since the specific gravities of the pulp fibers and the super absorbent polymers in the liquid mixture 51 are larger than the specific gravity of water in the treatment liquid 52, the pulp fibers, the super absorbent polymers, and the connected structure naturally sink.

In the present embodiment, as a preferred aspect, the treatment liquid 52 which is capable of dissolving the super absorbent polymers is an aqueous solution which includes the ozone containing gas which oxidatively decomposes the super absorbent polymers so that they can be dissolved. The ozone treatment process S36 (the continuous treatment process) further includes the delivery process of delivering continuously a plurality of bubbles of the ozone containing gas from the lower portion toward the upper portion of the treatment liquid 52. In such a preferred aspect of the present method, in the treatment liquid 52, the ozone containing gas is raised and the pulp fibers and the super absorbent polymers are lowered, that is, they form an opposed flow. Accordingly, the possibility of the pulp fibers and the super absorbent polymers coming into contact with the ozone containing gas can be increased. Further, the deeper the pulp fibers and the super absorbent polymers sink, the higher the concentration of the ozone containing gas the pulp fibers and the super absorbent polymers can come into contact with. Accordingly, the super absorbent polymers which could not have sufficiently been dissolved in the treatment liquid 52 only by the ozone containing gas with which the super absorbent polymers came into contact at the shallow portion in the treatment liquid 52, can be made to come into contact with the ozone containing gas with a high concentration at the deep portion in the treatment liquid 52. Thus, the super absorbent polymers can be reliably dissolved into the treatment liquid 52. Therefore, the super absorbent polymers can be reliably dissolved into the treatment liquid, whereby can be removed from the fibers.

In the present embodiment, as a preferred aspect, the above-mentioned delivery process includes the process of delivering the ozone containing gas in a state of microbubbles or nanobubbles. Note that microbubbles are bubbles with diameter of approximately 1 to 1000 μm, and preferably 10 to 500 μm, and nanobubbles are bubbles with diameter of approximately 100 to 1000 nm, and preferably 100 to 500 nm. The microbubbles or nanobubbles are such fine bubbles, and have a property that the surface area per unit volume is large and the rising speed in liquid is slow. Accordingly, in the present method, as a preferred aspect, such fine bubbles of ozone containing gas are delivered from the lower portion toward the upper portion of the treatment liquid 52 in the treatment tank 31.

On the other hand, the pulp fibers and the super absorbent polymers move from the upper portion toward the lower portion. At this time, since the fine bubbles have slow rising speed, the possibility that the bubbles come into contact with the pulp fibers can be increased. Further, since the occupation area of the fine bubbles in the surface of the pulp fibers is small, more bubbles can be made to come into contact with the surface of the pulp fibers. Accordingly, the pulp fibers, the super absorbent polymers, and the connected structure can be evenly wrapped with fine bubbles, and the contact area of these and the ozone containing gas can be further increased. Still further, more bubbles come into contact with the surface of the pulp fibers, whereby the sedimentations of the pulp fibers, the super absorbent polymers, and the connected structure are reduced by the buoyant force of bubbles, and the time during which these and the ozone containing gas that come into contact with can be increased. Thus, the super absorbent polymers can be reliably dissolved into the treatment liquid 52, whereby can be removed from the pulp fibers.

In the present embodiment, as a preferred aspect, the treatment liquid 52 is an acidic aqueous solution, and for example, is an acidic aqueous solution with pH of 2.5 or lower. In this case, even when the absorption capacity of the super absorbent polymers in the liquid mixture 51 partially remains, the absorption and swelling of the super absorbent polymers can be suppressed. Accordingly, the super absorbent polymers can be dissolved into the treatment liquid 52 in a short amount of time, and the super absorbent polymers can be more reliably moved. Especially, in a case in which the treatment liquid 52 is an ozone containing aqueous solution, ozone in the ozone containing aqueous solution can be made so that it is difficult to be inactivated, whereby the super absorbent polymers can be dissolved in a shorter amount of time so as to be dissolved, and the super absorbent polymers can be more reliably removed from the fibers.

Figure 3:
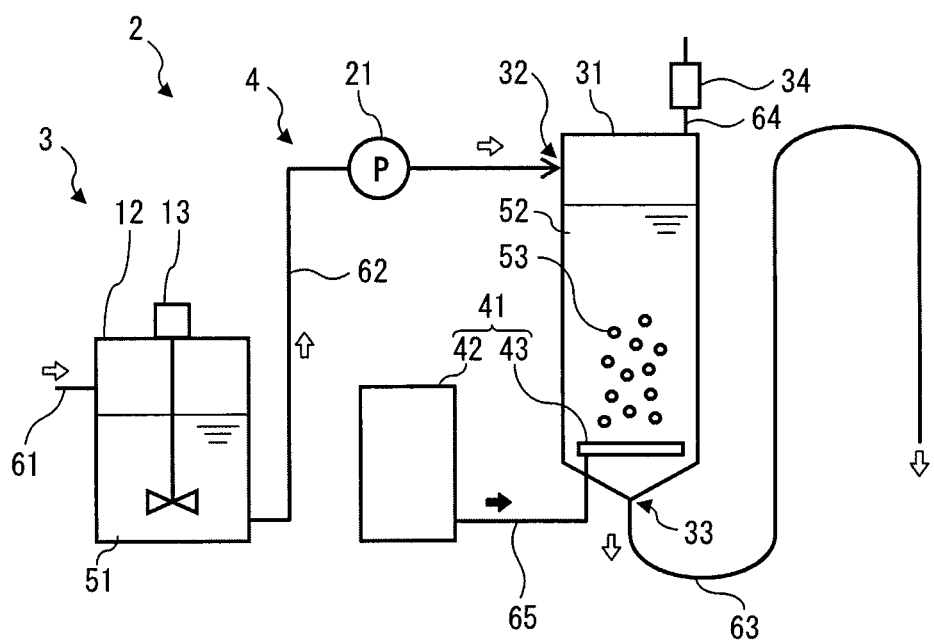
FIG. 3 is a schematic view which shows another configurational example of an apparatus of the ozone treatment process of FIG. 1.

Further, as another preferred embodiment, the configuration of the treatment tank 31 can be a configuration other than that shown in FIG. 2. FIG. 3 is a schematic view which shows another configurational example of the apparatus 2 of the ozone treatment process of FIG. 1. The apparatus 2 shown in FIG. 3 is different from the apparatus 2 shown in FIG. 2 in that the pipe 63 of the ozone treatment portion 4 has a continuous U-shaped pipe structure in which two U-shaped pipes are connected reversely and continuously to each other, and the delivery pump 22 is omitted. In such a case, when the pipe 63 is filled with the treatment liquid 52, and the height of the liquid surface of the treatment liquid 52 inside the treatment tank 31 is higher than the height of the liquid surface of the liquid inside the tank of the subsequent process connected by the pipe 63, the treatment liquid 52 is discharged to the tank of the subsequent process through the pipe 63, by the principle of siphon. Accordingly, before initiation of the process, by initially setting the height of the liquid surface of the treatment liquid 52 inside the treatment tank 31 the same as the height of the liquid surface of the liquid inside the tank of the subsequent process, and by the initiation of the process, when the liquid mixture 51 is supplied continuously into the treatment tank 31 in the first flow rate, the treatment liquid 52 is to be discharged to the tank of the subsequent process through the pipe 63 so as to satisfy "second flow rate=first flow rate", by the principle of siphon. Note that the height of the liquid surface of the liquid inside the tank of the subsequent process is to maintain the height before the initiation of the process even during the process. In this case, the delivery pump 22 is not necessary, and the control of the second flow rate of the delivery pump 22 is no longer necessary.

In the present embodiment, the separation process S13 may further include the fourth separation process S37 of separating the pulp fibers from the treatment liquid 52 which is discharged from the treatment tank 31, and the second drying process S38 of drying the separated pulp fibers.

In the fourth separation process S37, the method of separating the pulp fibers from the treatment liquid 52 which is discharged from the treatment tank 31 is not particularly limited, and for example, the method of letting the treatment liquid 52 including the pulp fibers for saccharification pass through, for example, a screen mesh with openings of 0.15 to 2 mm, may be mentioned. When the treatment liquid 52 including the pulp fibers for saccharification is made to pass through a screen mesh with openings of 0.15 to 2 mm, the waste water including the products by the oxidative decomposition of the super absorbent polymers passes through the screen. On the other hand, the pulp fibers for saccharification remain on the screen.

In the subsequent second drying process S38, the separated pulp fibers are dried in an atmosphere with a high temperature or by hot air, etc. The drying temperature is, for example, 105 to 210° C., and is preferably 110 to 190° C. The drying time is, although depending on the drying temperature, for example, 10 to 120 minutes, and is preferably 15 to 100 minutes. Accordingly, the solvent which remains on the surfaces of the pulp fibers is evaporated and removed, whereby pulp fibers in which mixed ratio of super absorbent polymers is extremely low and with high purity can be recovered. Thus, the configurational materials of the hygiene products can be efficiently recovered. Further, the pulp fibers can be sterilized (disinfected) by the atmosphere with a high temperature or by hot air, etc.

In the present disclosure, the pulp fibers for saccharification have a water contact angle of 20° or less, and has a water contact angle preferably of 15° or less, and more preferably of 10° or less. Accordingly, after the pulp fibers for saccharification which is manufactured by the above-mentioned manufacturing method, is dried and stored, the pulp fibers for saccharification can be easily dispersed in a saccharification aqueous solution. Incidentally, from the above-mentioned view point, the above-mentioned water contact angle of the pulp fibers for saccharification may be 0°.

The water contact angle of the pulp fibers for saccharification can be measured in the following manner.

(1) In a constant temperature and humidity chamber with a temperature of 20±5° C. and a humidity of 65±5% RH, an aluminum ring (with an outer diameter of 43 mm, an inner diameter of 40 mm, and a height of 5 mm) and the pulp fibers for saccharification which have been dried at 120° C. for 60 minutes are prepared, and are left still for 24 hours.

(2) 1.5 g of the pulp fibers for saccharification is filled evenly in the aluminum ring, and the pulp fibers for saccharification, together with the aluminum ring, are compressed for 1 minute by a pressure of 3 Mpa by using a pressing machine with a smooth bottom surface, whereby the surface of the recycled pulp fibers is smoothed.

(3) The water contact angle of the compressed pulp fibers for saccharification is measured in accordance with 6. Sessile drop method of JIS R 3257: 1999 "Wetability test method for substrate glass surface". As the contact angle measuring apparatus, the automatic contact angle measurer CA-V type manufactured by Kyowa Interface Science, Inc., may be mentioned. The above-mentioned water contact angle means the value after 200 ms, after dropping deionized water.

(4) The water contact angles are measured for 20 different samples, and the average value thereof is adopted.

In the present disclosure, the pulp fibers for saccharification have a lignin content ratio of 0.1 mass % or less, and have a lignin content ratio preferably of 0.08 mass % or less, and more preferably of 0.06 mass % or less. Accordingly, the pulp fibers for saccharification have excellent saccharification property.

The lignin content ratio of the pulp fibers for saccharification can be measured in accordance with the method described in pages 85 to 87 of "Soil diagnosis guidance" published in March, Showa 63, by Agriculture, forestry and fisheries department, Agriculture guidance division, of Ehime prefecture. Hereinbelow, the summary thereof is copied.

<Preparation of Reagents>

(1) In a constant temperature and humidity chamber with a temperature of 20±5° C. and a humidity of 65±5% RH, the pulp fibers for saccharification which have been dried at 120° C. for 60 minutes are prepared, and are left still for 24 hours.

(2) Commercially available lignin (95%) is prepared as a standard reagent.

(3) In a 500 mL beaker, 22.3 g of sodium pyrophosphate ($Na_4P_2O_5 \cdot 10H_2O$) is measured, approximately 400 mL of deionized water is added and sodium pyrophosphate is dissolved, whereby sodium pyrophosphate aqueous solution is made.

(4) In another 500 mL beaker, 10 g of sodium hydroxide is measured, approximately 200 mL of deionized water is added and sodium hydroxide is dissolved, whereby sodium hydroxide aqueous solution is made.

The sodium pyrophosphate aqueous solution and the sodium hydroxide aqueous solution are made to cool down, are added to 1 L volumetric flask, are made to constant volume with deionized water, whereby pyrophosphate extract liquid is made.

<Previous Operation>

(5) 2 g of lignin is measured in 100 mL Erlenmeyer flask A.

(6) 2 g of the pulp fibers for saccharification is measured in another 100 mL Erlenmeyer flask B.

(7) 20 mL of pyrophosphate extract liquid is added to each of Erlenmeyer flask A and Erlenmeyer flask B, and is shaken for 3 minutes.

(8) Erlenmeyer flask A and Erlenmeyer flask B are left still for 15 minutes, and thereafter, are filtered with a filter paper No. 6, whereby lignin filtrate and pulp fibers for saccharification filtrate are obtained.

<Analysis>

(9) By using a whole pipette, 5 mL of lignin filtrate is added to 50 mL volumetric flask, and is made to constant volume with deionized water (lignin 10,000 ppm).

(10) By using a measuring pipet, 1 mL, 2 mL, 5 mL and 10 mL of lignin filtrate with constant volume is respectively added to four 100 mL volumetric flasks, is made to constant volume with deionized water, whereby calibration solutions (100 ppm, 200 ppm, 500 ppm, and 1,000 ppm) are formed.

(11) Deionized water is set as blank, the transmittance of the calibration solutions is measured at a wavelength of 530 nm, and is converted to absorbance with reference to the absorbance conversion table shown in page 235.

(12) The calibration curve between the concentration of the calibration solutions and the absorbance is created.

(13) The transmittance of the pulp fibers for saccharification filtrate is measured by setting deionized water as blank, is converted to absorbance with reference to the absorbance conversion table shown in page 235, and lignin concentration is calculated from the calibration curve.

(14) From the lignin concentration, the lignin content ratio (mass %) is calculated.

Incidentally, the above-mentioned commercially available lignin (95%) may be changed to commercially available lignin (for example, lignin of Nacalai Tesque, Inc.) with different lignin concentration, etc.

In the manufacturing method of the present disclosure, the pulp fibers for saccharification have a beating degree reduction speed preferably of 300 mL or more, more preferably of 320 mL or more, still more preferably of 340 mL or more, and even more preferably of 360 mL or more. Accordingly, in the subsequent saccharification step, it is easy for the pulp fibers for saccharification to fluff when being applied with physical force, that is, to be increased in the surface area, whereby can be easily saccharified.

Incidentally, the above-mentioned beating degree reduction speed can be obtained by the manufacturing method of the present disclosure achieving the low lignin content ratio of the pulp fibers for saccharification, and the narrow distribution of the lignin content ratio, etc.

The above-mentioned beating degree reduction speed is measured in accordance with the following beating degree reduction test.

<Beating Degree Reduction Test>

(1) The pulp fibers for saccharification are beaten for one hour or longer, preferably for two hours, in accordance with Pulp—Beating method—Part 1: Beater method of JIS P 8221-1: 1998.

(2) After initiation of the beating, samples are taken every 20 minutes, and the beating degree (Canadian Standard freeness) of each sample is measured in accordance with Pulp—Freeness test method—Part 2: Canadian Standard freeness method of JIS P 8121-2:2012. Note that the test may be stopped when the beating degree of the samples is lower than 100 mL.

(3) Time (h) is plotted on the horizontal axis, and the beating degree (mL) is plotted on the vertical axis, so as to approximate the plots to a linear function by using the least square method, and the absolute value of the slope thereof is adopted as the beating degree reduction speed (mL/m).

Incidentally, the larger the value of the beating degree reduction speed, the reduction of the beating degree per unit time is fast, that is, meaning that it is easier for the pulp fibers for saccharification to be beaten (to fluff).

In the present disclosure, the pulp fibers for saccharification have an ash content ratio preferably of 0.65 mass % or less, more preferably of 0.50 mass % or less, still more preferably of 0.30 mass % or less, and even more preferably of 0.20 mass % or less. Accordingly, in a case in which the saccharification step is performed, for example, under the presence of a cellulase enzyme, it is difficult for the activity of the cellulase enzyme to be inhibited by metal ions.

The above-mentioned ash content ratio can be reduced by selecting, in the inactivation process S31 of inactivating the super absorbent polymers, an acid which can form a complex with metal ions included in an excrement, and especially citric acid, as the inactivation agent.

In the present description, ash means the amount of inorganic or non-flammable residue left after organics have been ashed, and ash content ratio means the ratio (mass ratio) of ash included in materials to be promoted. The above-mentioned ash content ratio is measured in accordance with "5. Ash test method" of "2. General test method" in Physiological treatment material standard. To be more specific, the ash content ratio is measured as follows.

(1) A platinum, quartz, or magnetic crucible is preheated at strong heat of 500 to 550° C. for 1 hour, allow the same to cool down, and the mass thereof is measured precisely.

(2) 2 to 4 g of the pulp fibers for saccharification which have been dried at 120° C. for 60 minutes is taken, is added into the crucible, the mass thereof is measured precisely, the lid of the crucible is removed or shifted if necessary, and while weakly heated initially, the temperature is gradually increased up to strong heat of 500 to 550° C. for more than 4 hours, so as to be ashed until no carbide remains.

(3) After allowing the same to cool down, the mass thereof is measured precisely. The residue is ashed again until the same reaches a constant weight, after allowing the same to cool down, the mass thereof is measured precisely, and the measured mass is regarded as the ash content ratio (mass %).

In the present embodiment, as a preferred aspect, before the ozone treatment process S36 (the continuous treatment process), the inactivation process S31 of, treating the mixture by using an aqueous solution which can inactivate the absorption capacity of the super absorbent polymers, whereby inactivating the absorption capacity of the super absorbent polymers in the mixture, and before the ozone treatment process S36 (the continuous treatment process), the first separation process S32 of separating the inactivated super absorbent polymers and the pulp fibers from the aqueous solution, are further included. In such a manner, in the present method, as a preferred aspect, in the inactivation process S31, the absorption capacity of the super absorbent polymers is suppressed by an aqueous solution which can inactivate the absorption capacity of the super absorbent polymers, whereby at the stage of the ozone treatment process S36 (the continuous treatment process) in the subsequent process, the super absorbent polymers can be dissolved more easily and in a shorter amount of time by the treatment liquid 52.

In the present embodiment, as a preferred aspect, in the inactivation process S31, the aqueous solution which can inactivate the absorption capacity of the super absorbent polymers is an acidic aqueous solution, and for example, is an acidic aqueous solution with pH of 2.5 or lower. In this manner, in the present method, as a preferred aspect, the aqueous solution which can inactivate the absorption capacity of the super absorbent polymers is an acidic aqueous solution, whereby the super absorbent polymers can be more easily inactivated, and at the stage of the inactivation process S31, the absorption capacity of the super absorbent polymers can be more reliably suppressed. Accordingly, at the stage of the ozone treatment process S36 (the continuous treatment process) in the subsequent process, the super absorbent polymers can be dissolved more easily and in a shorter amount of time by the treatment liquid.

Figure 4:
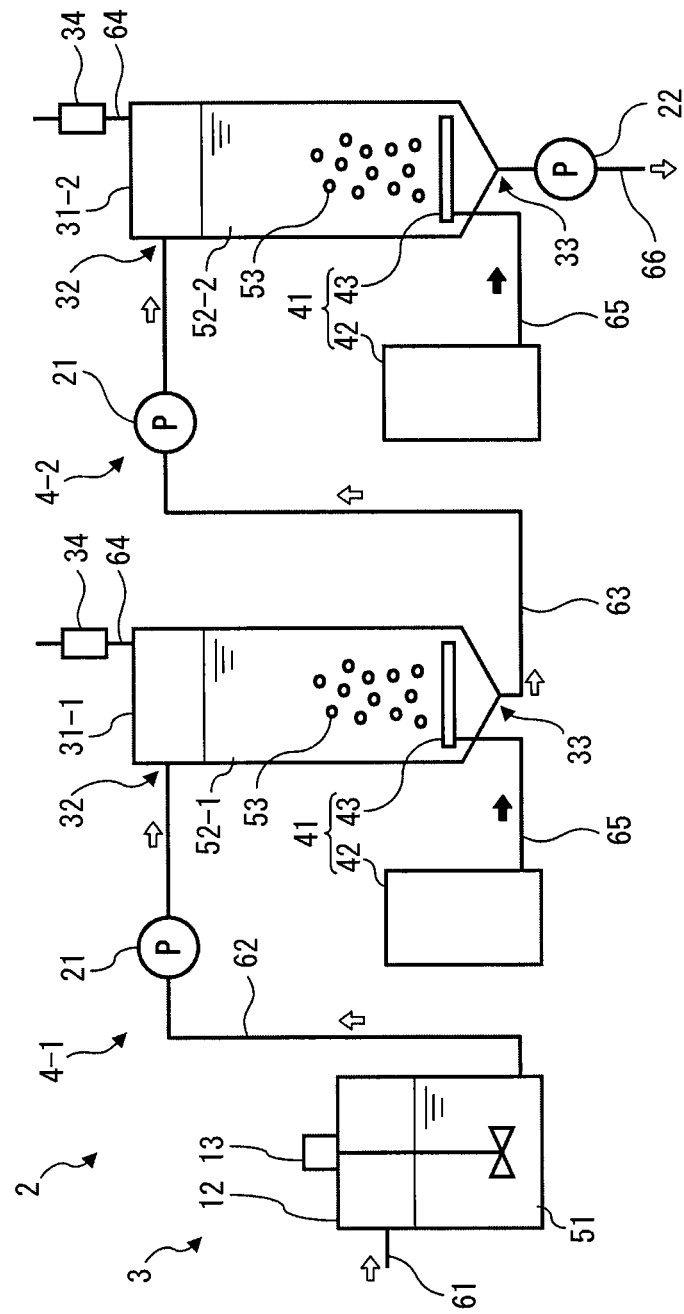
FIG. 4 is a schematic view which shows still another configurational example of an apparatus of the ozone treatment process of FIG. 1.

Further, as another preferred embodiment, the treatment tank 31 may include the first treatment tank 31-1 and the second treatment tank 31-2 which are at least connected to each other in series. FIG. 4 is a schematic view which shows still another configurational example of the apparatus 2 of the ozone treatment process of FIG. 1. The apparatus 2 of FIG. 4 is different from the apparatus 2 of FIG. 2 in that two ozone treatment portions 4 are joined in series, in other words, the first treatment tank 31-1 and the second treatment tank 31-2 are joined in series. In such a case, for example, the liquid mixture 51 is treated in multiple stages, such that the first treatment tank 31-1 is supplied with the liquid mixture 51 and discharges the first treated liquid (the treatment liquid 52-1 in the first treatment tank 31-1), and the second treatment tank 31-2 is supplied with the first treated liquid and discharges the second treated liquid (the treatment liquid 52-2 in the second treatment tank 31-2). In such a case, in comparison to the case of including one treatment tank 31 with large capacity, since treatment is performed by the new treatment liquid 52-1, 52-2 for each of the first and the second treatment tanks 31-1, 31-2, for example, the super absorbent polymers which could not be sufficiently dissolved in the first treatment tank (the treatment tank at the first stage) 31-1 can be easily dissolved by the second treatment tank (the treatment tank at the next stage) 31-2, etc., whereby the super absorbent polymers can be more reliably dissolved, and can be removed from the fibers.

In the present embodiment, as a preferred aspect, further in the material separation process Si, at the pretreatment process S11, the used hygiene products can be brought to the state of not being broken, etc., as they are, and of being extremely swollen by water without the inactivation of the super absorbent polymers. Accordingly, an extremely high internal pressure is generated inside the used hygiene products, whereby the used hygiene products can be brought to a state in which any portions of the surfaces are about to be torn. Then, in the disassembly process S12, by applying physical impact on the used hygiene products in such a state, any portions of the surfaces are torn, whereby the absorbent core inside erupts outside. Therefore, the used hygiene products can be disassembled into at least the films (the back sheet), and the absorbent core. At this time, since the films substantially maintain the original shape, the films can be easily separated from the absorbent core in the subsequent separation process S13. Accordingly, the configurational materials such as films, can be separated from other configurational materials without being broken, etc., and maintaining the shape as they are. Thus, the configurational materials such as films of the hygiene products can be recovered efficiently.

In the present embodiment, as a preferred aspect, by using terpene in removing the adhesive agents, the hot melt adhesive agent which joins the configurational materials of the hygiene products can be dissolved at a normal temperature. Accordingly, the hygiene products can be broken apart easily and neatly, whereby the pulp fibers and the super absorbent polymers are separated from the hygiene products, and the nonwoven fabric and films can be separated while maintaining individually the material form thereof. That is, the pulp fibers, the films, and the nonwoven fabric can be easily separately recovered without having to break the hygiene products and going through complicated separation processes. In a case in which limonene is used as terpene, as a secondary effect of limonene, since limonene has a refreshing citrus smell, the excrement-derived smell can be covered to a certain extent, and the burden of smell on workers and the adverse effects of smell in the neighborhood, etc., can be reduced. Since limonene is monoterpene and is similar in structure to styrene, limonene can dissolve styrene-based hot melt adhesive agents which are generally used in hygiene products. Since cleaning treatment of hygiene products in the normal temperature is possible, the energy cost can be reduced, and smell generation and diffusion can be suppressed. Terpene has a high cleaning effect of oil stains, and other than the dissolving effect of hot melt adhesive agents, in a case in which printing is provided in the films, the printing ink can also be decomposed and removed, whereby the films on which printing is provided can also be recovered as a plastic material with high purity.

Further, when an organic acid aqueous solution with pH of 2.5 or lower is used for inactivation of the super absorbent polymers, it is difficult to deteriorate the pulp fibers. Still further, when citric acid is used as the organic acid, by the chelating effect and the cleaning power of citric acid, removal effect of dirt components which derive from excrement can be expected. Still further, disinfection effect and deodorizing effect on alkaline smell can also be expected.

Further, by oxidatively decomposing the super absorbent polymers by ozone, it is possible to prevent contamination to the pulp fibers, and rapid increase of waste water by water absorption of the super absorbent polymers, etc. By adjusting the concentration of ozone, it is possible to perform oxidative decomposition of the super absorbent polymers and sterilization at the same time. Still further, in a case in which ozone is used, since no chlorinated chemicals are used at all, RPF (refuse derived paper and plastic fuel) with high quality which hardly damages combustion furnace can be manufactured from the recovered plastic materials. Since salt is not used during the treatment process, salt does not remain in the pulp fibers, whereby pulp fibers for saccharification with low ash and with high quality can be recovered.

The manufacturing method of the present disclosure may further include the saccharification step of saccharifying the pulp fibers for saccharification after the treatment liquid discharge step. As the above-mentioned saccharification step, although not particularly limited, saccharification methods known in the technical field are included. As the above-mentioned saccharification methods, for example, the methods described in Japanese Unexamined Patent Publication No. 2006-141244, Japanese Unexamined Patent Publication No. 2009-183211, Japanese Unexamined Patent Publication No. 2010-17084, Japanese Unexamined Patent Publication No. 2010-36058, and Japanese Unexamined Patent Publication No. 2013-202021, etc., may be mentioned.

As the above-mentioned saccharification step, as shown in FIG. 1, the dried pulp fibers for saccharification which are obtained in the second drying process S38, or the undried pulp fibers for saccharification which are obtained in the fourth separation process S37 may be subjected to the saccharification step, or alternatively, the treatment liquid 52 which includes the pulp fibers for saccharification that is obtained in the ozone treatment process S36 may be subjected to the saccharification step.

EXAMPLES

The pulp fibers for saccharification were manufactured in accordance with the method shown in FIG. 1 and FIG. 2, from a plurality of types of used diapers which have been collected from a care facility. The conditions related to the ozone treatment process S36 were as follows.

(i) liquid mixture 51
concentration: 1 mass % (concentration of the pulp fibers and the super absorbent polymers)
pH: 2.4
(ii) treatment tank 31
capacity: 60 L
height: 2.6 m
first flow rate: 2 L/minute
second flow rate: 2 L/minute
in-tank treatment time: 30 minutes
V/W: 100
$R_O/V$: 0.033
(iii) ozone containing gas
ozone concentration: 100 g/m³
form: nanobubbles Manufacturing Example 1

The inactivation process S31 was performed by using slaked lime, the ozone treatment process S36 was performed under the above-mentioned conditions, and the obtained pulp fibers for saccharification were dried at 120° C. for 60 minutes, whereby the pulp fibers for saccharification No. 1 were obtained.

Comparative Manufacturing Example 1

In the same manner as the Manufacturing example 1 other than not delivering the ozone containing gas in the ozone treatment process S36, the pulp fibers for saccharification No. 2 were obtained.

Comparative Manufacturing Example 2

NBKP virgin pulp fibers were set as the pulp fibers for saccharification No. 3.

Example 1, and Comparative Examples 1 and 2

The lignin content ratio (mass %), the water contact angle)(°, and the ash content ratio (mass %) of the pulp fibers for saccharification No. 1 to No. 3 were measured in accordance with the methods described in the present description. The results are shown in Table 1. Further, the beating degree reduction speed (mL/h) of the pulp fibers for saccharification No. 1 to No. 3, and the beating degree (mL) after having been beaten for a predetermined amount of time in the beating degree reduction test were measured in accordance with the beating degree reduction test described in the present description. The results are also shown in Table 1.

The pulp fibers for saccharification No. 1 to No. 3 were subjected to saccharification in accordance with the following cellulase method. The residual ratio (mass %) of the residue after saccharification is shown in Table 1.

<Cellulase Method>

(1) Approximately 3 g of the pulp fibers for saccharification was weighed [mass: $m_0$ (g)], and thereafter, 160 mL of distilled water and 40 mL of 0.5 M glycine-hydrochloric acid buffer (pH 4.0) were added, and further, 1 g of Cellulase Onozuka and 1 g of Cellulase Y-NC were added.

(2) The prepared sample was kept at 45° C., and was stirred for 3 hours.

(3) After treatment, the sample was neutralized with sodium hydrogen carbonate, and was added with calcium chloride.

(4) The supernatant was discarded, distilled water was added to the precipitate to be stirred, and the supernatant was discarded. This operation is repeated until the supernatant becomes transparent (5) The precipitate was filtered with glass fiber filter paper, and thereafter was dried at 110° C. for 2 hours or more, after being let to cool down in a desiccator, the precipitate was weighed [mass: $m_1$ (g)].

Incidentally, the residual ratio of the residue after saccharification is calculated by the following formula.

$$\text{Residual ratio (\%)} = 100 \times m_1/m_0$$

The results are also shown in Table 1.

When the residue after saccharification was confirmed, the residue of the pulp fibers for saccharification No. 1 and No. 3 was configured by the pulp fibers, and the residue of the pulp fibers for saccharification No. 2 was configured by the pulp fibers and the super absorbent polymers.

In the above-mentioned Cellulase method, since the super absorbent polymers are not decomposed in principle, it can be understood that the pulp fibers for saccharification No. 1 (residual ratio: 59 mass %) can be more easily saccharified than the NBKP virgin pulp fibers (residual ratio: 66 mass %).

TABLE 1

| | Example No. | | |
|---|---|---|---|
| | Example 1 | Comparative example 1 | Comparative example 2 |
| Pulp fibers for saccharification No. | No. 1 | No. 2 | No. 3 |
| Inactivation | Slaked lime | Slaked lime | — |
| Ozone treatment | Performed | Not performed | — |
| Lignin content ratio (mass %) | <0.10 | 0.15 | 0.16 |
| Water contact angle (°) | 0 | —[a] | 13.9 |
| Ash content ratio (mass %) | 0.15 | 16 | 0.12 |
| Beating degree reduction speed (mL/h) | 360 | — | 275 |
| Beating degree (mL)/time (minute) | 138/120 | — | 270/120 |
| Residual ratio (mass %) of residue after saccharification | 59 | 76 | 66 |

[a] There were much foreign matter, and could not be measured.

REFERENCE SIGNS LIST

31 treatment tank
32 liquid mixture supply port
33 treatment liquid discharge port
43 ozone containing gas supply port
51 liquid mixture
52 treatment liquid
53 ozone containing gas
S36 ozone treatment process

The invention claimed is:

1. A method of manufacturing pulp fibers for saccharification from pulp fibers of used hygiene products, comprising steps of:

a preparation step of preparing a treatment tank which includes a liquid mixture supply port, and a treatment liquid discharge port and an ozone containing gas supply port that are arranged below the liquid mixture supply port, a liquid mixture supply step of supplying a liquid mixture which includes super absorbent polymers and the pulp fibers that derive from the used hygiene products and water, from the liquid mixture supply port to the treatment tank, an ozone containing gas supply step of supplying ozone containing gas from the ozone containing gas supply port to a treatment liquid in the treatment tank, wherein the ozone concentration in the ozone containing gas is 40 to 200 g/m$^3$ to cause the decomposition of the super absorbent polymers, a pulp fibers for saccharification formation step of forming the pulp fibers for saccharification from the pulp fibers while dissolving at least a portion of the super absorbent polymers in the treatment liquid, by, in the treatment tank, raising the ozone containing gas while lowering the super absorbent polymers and the pulp fibers so as to make the ozone containing gas come into contact with the super absorbent polymers and the pulp fibers, and a treatment liquid discharge step of discharging the treatment liquid which includes the pulp fibers for saccharification from the treatment liquid discharge port, wherein the pulp fibers for saccharification have a lignin content ratio of 0.1 mass % or less.

2. The method according to claim 1, wherein the pulp fibers for saccharification have a water contact angle of 20° or less.

3. The method according to claim 1, wherein the pulp fibers for saccharification have a beating degree reduction speed of 300 mL/h or more.

4. The method according to claim 1 wherein in the pulp fibers for saccharification formation step, the ozone containing gas is supplied from the ozone containing gas supply port as microbubbles or nanobubbles.

5. The method according to claim 1, wherein the treatment liquid is acidic.

6. The method according to claim 1, further comprising an inactivation step of inactivating the super absorbent polymers by an acid, before the liquid mixture supply step.

7. The method according to claim 6, wherein the acid is an acid which can form a complex with metal ions included in an excrement.

8. The method according to claim 1, wherein the pulp fibers for saccharification have an ash content ratio of 0.65 mass % or less.

9. The method according to claim 1, wherein in the liquid mixture supply step, the liquid mixture is supplied continuously from the liquid mixture supply port to the treatment tank in a first flow rate, and in the treatment liquid discharge step, the treatment liquid is discharged continuously from the treatment liquid discharge port in a second flow rate.

10. The method according to claim 1, further comprising a saccharification step of saccharifying the pulp fibers for saccharification, after the treatment liquid discharge step.

11. A method of manufacturing pulp fibers for saccharification from pulp fibers of used hygiene products according to claim 1, wherein the ozone concentration in the treatment liquid is 1 to 50 mass ppm.

12. A method of manufacturing pulp fibers for saccharification from pulp fibers of used hygiene products according to claim 1, wherein a flow rate R0 (L/minute) of the ozone containing gas and a volume V (L) of the treatment liquid inside the treatment tank satisfy $0.01 \leq R_O/V \leq 1.25$.

13. A method of manufacturing pulp fibers for saccharification from pulp fibers of used hygiene products according to claim 1, wherein a CT value which is a product of an ozone concentration (mass ppm) in the treatment liquid and an in-tank treatment time (minute) is 100 to 6000 ppm·minute.

* * * * *